United States Patent
Masuo

(10) Patent No.: US 7,203,536 B2
(45) Date of Patent: Apr. 10, 2007

(54) METHOD AND APPARATUS FOR THE DETERMINATION OF BODY COMPOSITION USING BIOELECTRIC IMPEDANCE MEASUREMENTS IN A DEPTH DIRECTION

(75) Inventor: Yoshihisa Masuo, Kyoto (JP)

(73) Assignee: Physion Co., Ltd., Kyoto (JP)

( * ) Notice: Subject to any disclaimer, the term of this patent is extended or adjusted under 35 U.S.C. 154(b) by 397 days.

(21) Appl. No.: 10/380,241

(22) PCT Filed: Sep. 17, 2001

(86) PCT No.: PCT/JP01/08080

§ 371 (c)(1),
(2), (4) Date: Mar. 13, 2003

(87) PCT Pub. No.: WO02/24069

PCT Pub. Date: Mar. 28, 2002

(65) Prior Publication Data

US 2003/0176808 A1    Sep. 18, 2003

(30) Foreign Application Priority Data

Sep. 19, 2000   (JP)  ............................ 2000-283073

(51) Int. Cl.
*A61B 5/05* (2006.01)

(52) U.S. Cl. ..................................... 600/547

(58) Field of Classification Search ............. 600/547, 600/506, 536; 606/32, 34, 41
See application file for complete search history.

(56) References Cited

U.S. PATENT DOCUMENTS

| | | | | |
|---|---|---|---|---|
| 4,548,211 A | * | 10/1985 | Marks | ........................ 600/507 |
| 4,617,939 A | * | 10/1986 | Brown et al. | ................ 600/547 |
| 4,895,163 A | * | 1/1990 | Libke et al. | ................. 600/547 |
| 4,949,727 A | * | 8/1990 | Yamazaki et al. | ........... 600/547 |
| 5,353,802 A | * | 10/1994 | Ollmar | ....................... 600/547 |
| 5,544,662 A | * | 8/1996 | Saulnier et al. | ............. 600/547 |
| 5,560,372 A | * | 10/1996 | Cory | .......................... 600/554 |
| 5,720,296 A | * | 2/1998 | Cha | ........................... 600/554 |
| 6,408,204 B1 | * | 6/2002 | Hirschman | .................. 600/547 |

(Continued)

FOREIGN PATENT DOCUMENTS

EP    1 027 860 A1    8/2000

(Continued)

*Primary Examiner*—Max F. Hindenburg
*Assistant Examiner*—Michael Apanius
(74) *Attorney, Agent, or Firm*—Oliff & Berridge, PLC

(57) ABSTRACT

A bioelectrical impedance apparatus and method includes a pair of current-carrying electrodes and a pair of measuring electrodes are rectilinearly arranged on a living body surface so that the measuring electrode having a smaller area than the other measuring electrode is placed very close to the current-carrying electrode having a smaller area than the other current-carrying electrode. The potential of the measuring electrode is substantially equal to the potential at a contact position of the current-carrying electrode, and the potential of the measuring electrode is substantially equal to the potential at a deepest position of a vertical part inside the living body. When a constant current flows between the current-carrying electrodes, a voltage between the measuring electrodes is measured by a detector so that a bioelectrical impedance of the vertical part may be calculated from a current, and a potential difference between upper and lower ends of the vertical part.

7 Claims, 16 Drawing Sheets

U.S. PATENT DOCUMENTS

2001/0034491 A1* 10/2001 Benson et al. .............. 600/547

FOREIGN PATENT DOCUMENTS

| JP | B2 5-49050 | 7/1993 |
| JP | A 7-51242 | 2/1995 |
| JP | A 9-51883 | 2/1997 |
| JP | A 11-507858 | 7/1999 |
| JP | A 11-309123 | 11/1999 |
| JP | A 2000-14655 | 1/2000 |
| JP | A 2000-229072 | 8/2000 |

* cited by examiner (a)

(b)

(c)

(a)

(b)

(a)

(b)

METHOD AND APPARATUS FOR THE DETERMINATION OF BODY COMPOSITION USING BIOELECTRIC IMPEDANCE MEASUREMENTS IN A DEPTH DIRECTION

TECHNICAL FIELD

The present invention relates to a bioelectrical impedance measurement method for obtaining various kinds of information about internal panniculus, such as fatty tissue, muscular tissue or osseous tissue, of such living bodies as human beings, livestock or other animals, to a measurement apparatus using the above method, and to a health management guideline advising apparatus using the measurement apparatus.

BACKGROUND ART

Conventionally, the commonest method in health management concerning obesity or other body conditions is to measure the body weight. Nowadays, obesity is not regarded simply as a body type, but people are looking at indices for measuring obesity. One such index is the body fat mass, which indicates the mass of subcutaneous fat and/or visceral fat; another is the body-fat ratio, which indicates the ratio of body fat to body weight.

For many years, measurement of body fat was complex and time consuming. The subject had to be completely submerged under water to measure the underwater body weight and to calculate the specific gravity. On the other hand, however, new and simpler measurement methods are used, which enable us to estimate a result that has a close correlation with the result obtained by conventional methods. Some of these methods use ultrasonic waves, some others use near infrared, and the most common methods use the bioelectrical impedance.

Many bioelectrical impedance measurement methods widely used are based on the measurement principle called the "four-electrode method". Referring to FIG. 27, a bioelectrical impedance measurement method based on the four-electrode method is described below.

According to this method, a pair of current-carrying electrodes $1a$, $1b$ and a pair of measuring electrodes $2a$, $2b$ are attached to the surface of a living body 5 so that the measuring electrodes $2a$, $2b$ are placed between the current-carrying electrodes $1a$, $1b$. The current-carrying electrodes $1a$, $1b$ are connected to a radio frequency current source 3 to supply constant radio frequency current i through the living body 5. The voltage (potential difference) produced thereby is measured by a detector 4 connected to the measuring electrodes $2a$, $2b$. If the inside of the living body 5 is homogeneous, it can be assumed that the current is almost evenly distributed at positions distant from the current-carrying electrodes, $1b$. Therefore, by placing the measuring electrodes $2a$, $2b$ away from the current-carrying electrodes $1a$, $1b$ to a predetermined extent, it is possible to obtain the bioelectrical impedance of a part $5a$ horizontally extending deep in the living body. Also, by setting the input impedance of the detector 4 adequately higher than the impedance of the measuring electrodes $2a$, $2b$, the influence of the impedance of the electrodes can be eliminated, so that the measurement can be performed accurately.

The bioelectrical impedance measurement method using the four electrodes is applied to various kinds of body composition measurement apparatuses described in documents and/or available on the market. For instance, the Japanese Unexamined Patent Publication No. H7-51242 discloses an apparatus having a pair of grips to be held by the hands, each grip provided with a current-carrying electrode and a measuring electrode. The electrodes are located so that, when the subject holds the grips with the hands, the current-carrying electrode contacts the hand at a part close to the fingers and the measuring electrode contacts the hand at a part dose to the wrist. Then, based on the bioelectrical impedance measured there by, the apparatus estimates various kinds of information about the living body, such as total internal body fat, lean body mass, body-fat ratio, total body water or basal metabolism rate. Also, the Japanese Examined Patent Publication No. H5-49050 discloses an apparatus constructed so that the electrodes contact the bottoms of the feet when the subject puts the feet on it. This apparatus can simultaneously measure the weight and the body fat.

The four-electrode method is widely used because, despite its easiness, it provides high accuracy in the measurement of bioelectrical impedance. As is clear from FIG. 27, however, the method has such a theoretical limit that it can measure the bioelectrical impedance of only the parallel constitution of a large area inside the living body 5 between the two measuring electrodes $2a$, $2b$, that is, the internal panniculus extending parallel to the surface of the living body 5. Therefore, it is essentially impossible to obtain information about the living body in the depth direction (i.e. the cross-sectional direction of the internal panniculus) below the surface, such as the local thickness of the subcutaneous fat or the thickness of the visceral fat.

By the body composition measurement apparatus using the above-described bioelectrical impedance measurement according to the four-electrode method, the bioelectrical impedance is measured along the current path between the two hands, between the two feet or between one hand and one foot, to estimate the lean body mass. Further, the body fat mass is also estimated using supplementary data relating to body-build, such as the height or the weight of the subject. By this apparatus, a part of the current path goes through the abdomen, whose cross-sectional area is a good deal larger than that of a leg or an arm. This means that the leg or the arm makes a relatively large contribution to the bioelectrical impedance, while the abdominal subcutaneous fat and the intra-peritoneal fat (visceral fat) make a relatively small contribution. Thus, the measurement result poorly reflects an increase or decrease of the abdominal subcutaneous fat or the intra-peritoneal fat, so that the result is not reliable.

Even without measuring the bioelectrical impedance, the information about the living body in the depth direction below the surface of the living body can be obtained with other apparatuses, such as X-ray computed tomography (CT) scanner or magnetic resonance imaging (MRI) apparatus. These apparatuses, however, are very large and very expensive, and they immobilize the subject for a long time. Thus, the subject is forced to suffer physically, mentally and economically. Further, they cannot be used by ordinary people in everyday life for health management or health maintenance.

The present invention has been achieved in view of the above problems, and its main object is to propose a bioelectrical impedance measurement method and apparatus, which give the subject same or less burden as that by the currently practiced measurements of bioelectrical impedance according to the four-electrode method, and which can measure the bioelectrical impedance in the depth direction inside of the living body, which has been difficult to measure by conventional methods.

Another object of the present invention is to propose a measurement apparatus, which uses the result of the measurement of the bioelectrical impedance in the depth direction inside the living body to obtain such information about the living body that is difficult to measure by conventional methods, and to present that information to the subject or to the examiner. Examples of the aforementioned information are the thickness of subcutaneous fat, the steatosis (or fatty change) of muscular tissue, the strength or thickness of osseous tissue (such as cortical bone density or cancellous bone density), and the steatosis of bone marrow cells inside the bone.

Still another object of the present invention is to improve the accuracy of the body composition measurement apparatuses using the conventional four-electrode method, and to propose a health management guideline advising apparatus, which can provide very useful information for guiding health management.

DISCLOSURE OF THE INVENTION

By the conventional four-electrode method, the current-carrying electrodes are attached away from the measuring electrodes so that an ideal flow of radio frequency current is generated, that is, so that the current adequately spreads out and uniformly flows inside the living body, as explained above. In studying the method of measuring the bioelectrical impedance for a long time, the inventor of the present application has come to an idea that is the opposite of the conventional idea. That is, the inventor aimed to measure the potential difference at a part below or nearly below the current-carrying electrode where the current flows almost perpendicular to the surface of the living body, i.e. at a part shallower than the part where the current path becomes almost horizontal.

According to the idea a new method of measuring bioelectrical impedance has been invented, where (1) one of the current-carrying electrodes is designed to generate a concentrated flow of current with high density in the depth direction of the living body below the electrode, and a measuring electrode is placed close to the current-carrying electrode to measure a voltage that is almost equal to the voltage at the contact part of the current-carrying electrode; and (2) while the current is flowing through the living body from the surface of the living body along the depth direction and generating equipotential surfaces, another measuring electrode is placed at a point on the surface of the living body where an equipotential surface emerges, to measure a voltage almost equal to the voltage at a certain position in the depth direction; or (3) with the measuring electrode placed in the same position as in (1), the current-carrying electrode placed close to the measuring electrode is moved away to measure a voltage almost equal to the voltage at a certain position in the depth direction below the measuring electrode, and (1) is combined with (2) or (3) to obtain a potential difference between the upper and lower ends of a predetermined part extending in the depth direction, and the bioelectrical impedance is calculated from the potential difference and the current.

That is, the present invention proposes a bioelectrical impedance measurement method for measuring a bioelectrical impedance relating to information about the inside of a living body from an electrical signal measured on a surface of the living body, which includes the following steps of:

attaching a set of current-carrying electrodes, including a first electrode having a small contact area and a second electrode to the surface of the living body apart from each other by preset distances, to generate a flow of radio frequency current inside the living body;

measuring a potential difference generated with the radio frequency current between a first part close to the first electrode on the surface of the living body and a second part away from the first part by a distance equal to or greater than a preset distance; and calculating the bioelectrical impedance in the depth direction below the contact part of the first electrode and its proximity, based on the potential difference and the value of the radio frequency current.

Further, to embody the above measurement method, the present invention proposes a bioelectrical impedance measurement apparatus for measuring a bioelectrical impedance relating to information about the inside of a living body from an electrical signal measured on the surface of the living body, which includes:

a) a set of current-carrying electrodes to be attached to the surface of the living body set apart from each other by predetermined distances, including a first electrode having a small contact area to generate a concentrated flow of current with high density, and a second electrode;

b) a radio frequency current supplying the means for generating a flow of radio frequency current inside the living body through the first and second current-carrying electrodes;

c) measuring electrodes attached to the surface of the living body, including a first electrode located close to the contact part of the first current-carrying electrode and a second electrode located away from the first measuring electrode by a distance equal to or greater than a predetermined distance;

d) a voltage measuring means for measuring the potential difference generated with the radio frequency current between the first and second measuring electrodes; and e) a calculating means for calculating the bioelectrical impedance in the depth direction below the contact part of the first current-carrying electrode and its proximity, based on the potential difference and the value of the radio frequency current.

In the bioelectrical impedance measurement method or apparatus according to the present invention, the first current-carrying electrode is required to have a contact area small enough to generate a concentrated flow of current with high density below the electrode. The second current-carrying electrode, however, is preferably designed to have a large contact area because of the reason explained below.

In the bioelectrical impedance measurement method or apparatus according to the present invention, a radio frequency current supplying means supplies a constant radio frequency current at a preset frequency between the fist and second current-carrying electrodes. If the second current-carrying electrode has a large contact area as described above, the current in the living body can easily penetrate into the depths, and flows horizontally with a stable current density distribution. Below the first current-carrying electrode, on the other hand, the current is concentrated because the contact area of the fist current-carrying electrode is small, so that the current path with considerably high current density in the cross-sectional area is formed in the depth direction almost perpendicular to the surface of the living body. The potential at the first part close to the contact part of the first current-carrying electrode is almost equal to the potential on the surface of the living body or at a part exclusive of the cutaneous tissue layer. Further, inside the living body, equipotential surfaces are formed corresponding to the potentials along the current path in the depth direction, and the equipotential surfaces emerge on the surface of the living body. This means that, the potential measured at the second part, which is set apart from the first part by a preset distance, is equal to the potential at a certain position in the depth direction of the current path that is measured. Therefore, the potential difference between the first part and the second part is equivalent to the potential difference between the upper and lower ends of a certain region extending along the current path in the depth direction. Thus, it is possible to measure the bioelectrical impedance in the depth direction, e.g. in the direction traversing the tissue layers of the living body immediately below the skin, below the contact part of the first current-carrying electrode and its proximity.

The measurement of the potential difference between the first part and the second part can be carried out in various modes. By the simplest mode, the voltage is directly measured with a detector provided between the first measuring electrode attached close to the first current-carrying electrode, i.e. the first pat, and the second measuring electrode attached to the second part (see FIG. 1). By this mode, the current needs to be supplied only once to measure the voltage, so that time and labor required for the measurement is reduced.

By another possible mode, a reference electrode is provided at a third part on the surface of the living body, apart from the first part and the second part, the voltage between the first part and the third part and the voltage between the second part and the third part are measured, and the difference between the two voltages is calculated (see FIG. 3). In this case, the second current-carrying electrode may be used as the reference electrode provided at the third part, or the reference electrode may be provided separately.

It is preferable to arrange the first and second current-carrying electrodes and the voltage-measuring electrodes almost rectilinearly on the surface of the living body. It is particularly preferable to place the first measuring electrode close to the first current-carrying electrode on an extension of the straight line drawn between the first current-carrying electrode and the second current-carrying electrode, and to place the second measuring electrode away from the first measuring electrode by a distance almost the same as the distance between the first current-carrying electrode and the second current-carrying electrode. With respect to both the current-carrying electrodes and the measuring electrodes, the minimum distance between the first electrode and the second electrode is determined according to the thickness of the living body and the depth of the measurement. By this construction, the current-carrying electrodes and the measuring electrodes are arranged axisymmetrical, where the reciprocity theorem allows the connections to be switched so that the voltage-detecting means is connected to the current-carrying electrodes and the current supplying means is connected to the measuring electrodes (see FIG. 2). Use of the results of measurements performed twice with the connections switched as described above improves the accuracy of the measurement. Further comparison of the two results makes it possible to obtain additional information other than the bioelectrical impedance of the cult concentration part in the depth direction that is common to both the measurements; for example, the difference in the bioelectrical impedance of the parallel constitution of the horizontally extending internal panniculus can be obtained.

It is further possible to place one or more measuring electrodes between the first measuring electrode and the second measuring electrode to measure the voltages between these electrodes. This construction makes it possible to measure the bioelectrical impedances of the regions located at different levels in the depth direction just below or nearly below the contact part of the first current-carrying electrode, so that detailed information about the living body can be obtained with high accuracy.

The present invention further proposes another bioelectrical impedance measurement method for measuring bioelectrical impedance relating to information about the inside of a living body from an electrical signal measured on the surface of the living body, having:

a fist measurement mode wherein a set of current-carrying electrodes, including a first electrode with a small contact area and a second electrode, are attached to the surface of the living body, set apart from each other by predetermined distances, to generate a flow of radio frequency current in the living body between the first electrode and the second electrode; and a second measurement mode wherein a flow of radio frequency current is generated between the second electrode and a third electrode attached to the surface of the living body on an extension of the straight line drawn between the first electrode and the second electrode, where the extension is at the side of the first electrode, and the method includes the following steps of:

measuring the voltage on the surface of the living body between a part around the first electrode and the contact part of the second electrode or its proximity for each of the first and second measurement modes, and calculating the voltage difference between the two modes; and calculating the bioelectrical impedance in the depth direction below the contact part of the first electrode and its proximity, based on the voltage difference and the value of the radio frequency current.

Further, to embody the above-described bioelectrical impedance measurement method, the present invention proposes a bioelectrical impedance measurement apparatus for measuring bioelectrical impedance relating to information about the inside of a living body from an electrical signal measured on a surface of the living body, which includes:

a) a set of current-carrying electrodes to be attached to the surface of the living body set apart from each other by predetermined distances, including a first current-carrying electrode with a small contact area, a second current caring electrode, and a third current-carrying electrode attached to the surface of the living body on an extension of the straight line drawn between the first current-carrying electrode and the second electrode, where the extension is on the same side as the fast current-carrying electrode;

b) a radio frequency current supplying means for generating a flow of radio frequency current in the living body between the fiat current-carrying electrode and the second current-carrying electrode in a first measurement mode, and for generating a flow of radio frequency current in the living body between the second current-carrying electrode and the third current-carrying electrode in a second measurement mode;

c) measuring electrodes including a first measuring electrode attached close to the first current-carrying electrode on the surface of the living body, and a second measuring electrode attached to the contact part of the second current-carrying electrode or its proximity;

d) a voltage measuring means for measuring the voltage between the first measuring electrode and the second measuring electrode for each of the first and second measurement mode, and for calculating the voltage difference between the two modes; and e) a calculating means for calculating the bioelectrical impedance in the depth direction below the contact part of the first current-carrying electrode and its proximity, based on the voltage difference and the value of the radio frequency current.

By the bioelectrical impedance measurement method and apparatus according to the present invention, the potential difference between the first measuring electrode and the second measuring electrode is measured in two modes. In the first mode, the cent flows through the first current-carrying electrode located close to the fist measuring electrode, so that the current is concentrated in the depth direction under the part to be measured; in the second mode, the current does not flow through the first current-carrying electrode but flows almost horizontally in the depths below the fist current-carrying electrode (see FIG. 6). The voltage obtained in the first mode is almost equal to the potential at the contact part of the first current-carrying electrode, and the voltage obtained in the second mode is almost equal to the potential at a certain depth below the first current-carrying electrode. Therefore, the difference between the two voltages is equivalent to the potential difference between the upper and lower ends of a certain region extending along the current path in the depth direction, as in the above-described measurement method and measurement apparatus. From this it is possible to calculate the bioelectrical impedance in the depth direction below the contact part of the first current-carrying electrode and its proximity.

By the bioelectrical impedance measurement method and apparatus according to the present invention, it is possible to obtain information about the living body in the depth direction below the skin of the subject by simply attaching or touching predetermined electrodes to parts of the surface of the skin, as in the case of the conventional four-electrode method. For example, the thickness of the subcutaneous fat the thickness of the muscular tissue, the thickness of the osseous tissue, etc., can be measured. It is also possible to estimate information relating to health guidelines, such as the steatosis of muscular tissue or other indices of the health of muscular tissue, the progress of osteoporosis or other indices of the health of osseous tissue, the steatosis of bone marrow cells or other indices of the health of bone marrow cells, etc. Conventionally, these kinds of diagnoses and examinations required a large system. According to the present invention, on the other hand, the same diagnosis and examination can be conducted easily and with high accuracy, imposing little mental, physical or economic burden on the subject. The apparatus can be made low-priced, small and light, so that it can be preferably used for everyday health management and maintenance.

Instead of being used independently, the bioelectrical impedance measurement method according to the present invention may be combined with the conventional four-electrode measuring method. This combination provides a wider range of measurement and greatly improves the accuracy of the result in the measurement of body-fat ratio, etc. The combination with the four-electrode method imposes less burden on the subject than is found with conventional methods, and can be achieved without greatly increasing the production costs of the apparatus.

BRIEF DESCRIPTION OF THE DRAWINGS

FIG. 1A is a plan view of the surface of a living body, FIG. 1B is the sectional view at line A–A' in FIG. 1A, and FIG. 1C is an enlarged view of the main part of FIG. 1B.

FIG. 15A is a plan view, and FIG. 15B is the sectional view at line B–B'.

BEST MODES FOR CARRYING OUT THE INVENTION

[An Embodiment of Measurement Method]

Figure 1:
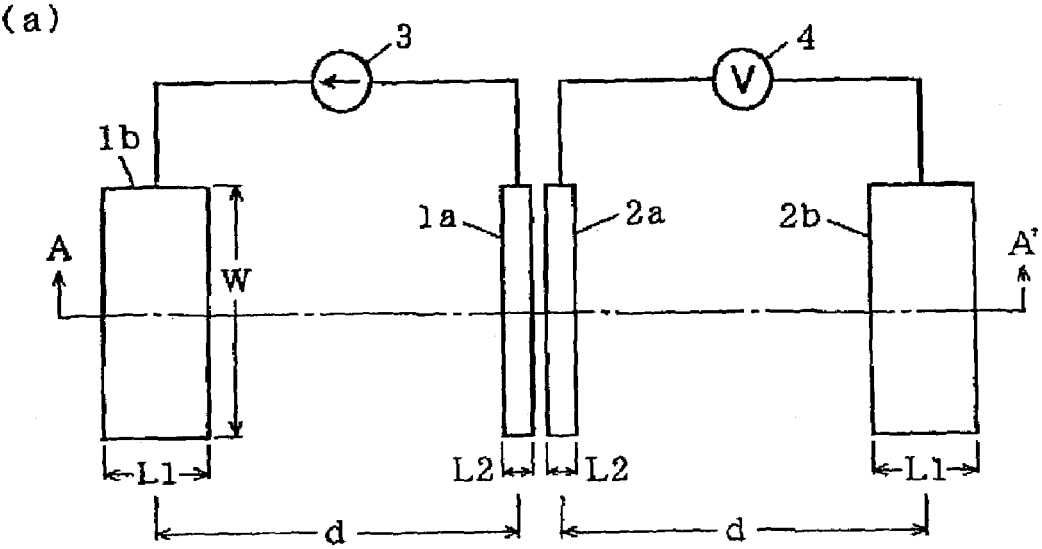
FIGS. 1A–1C show the most basic arrangement of the electrodes in the bioelectrical impedance measurement method according to the present invention, where
Figure 1:
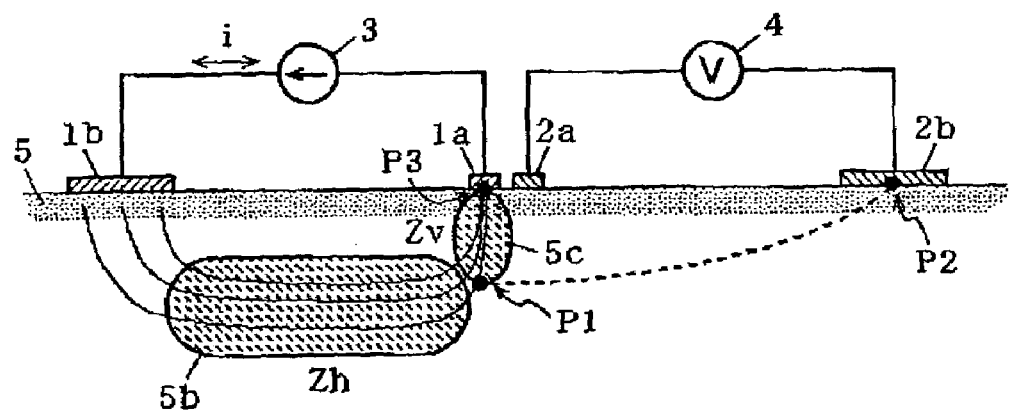
Figure 1:
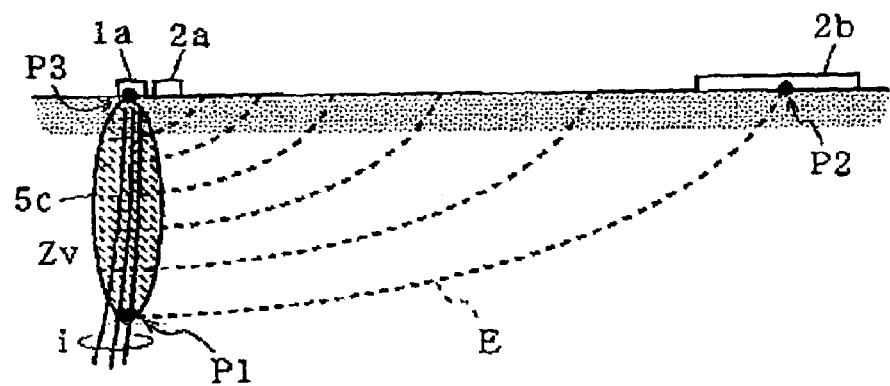

First, the principle of the bioelectrical impedance measurement method according to the present invention is explained.

FIGS. 1A–1C show the most basic arrangement of the electrodes in the bioelectrical impedance measurement method according to the present invention, where FIG. 1A is a plan view of the surface of a living body, FIG. 1B is the sectional view at line A–A' in FIG. 1A, and FIG. 1C is an enlarged view of the main part shown in FIG. 1B.

The electrodes for supplying radio frequency current consist of a first current-carrying electrode 1a and a second current-carrying electrode 1b having different areas. Similarly, the electrodes for measuring voltage consist of a first measuring electrode 2a and a second measuring electrode 2b having different areas. The first current-carrying electrode 1a and the first measuring electrode 2a are in the form of a rectangular strip having size of L2×W, and the second current-carrying electrode 1b and the second measuring electrode 2b are in the form of a rectangular strip having size of L1×W, where L1>>L2. As shown in FIG. 1A, these four electrodes 1a, 1b, 2a, 2b are arranged rectilinearly so that they are symmetrical with respect to the center line dividing the gap between the first current-carrying electrode 1a and the first measuring electrode 2a. The rectangular strip form of the electrodes provides the following effects: the measurement condition can be defined by the direction of arranging the electrodes (i.e. in the width direction of the electrode); the length of the electrode provides necessary and sufficient contact for the electrode to avoid contact failure and to reduce the resistance of the electrode.

Between the first current-carrying electrode 1a and the second current-carrying electrode 1b, a radio frequency current source 3 (referred to as the "current source" hereinafter) supplies a constant current of value i at a preset frequency. Between the first and second measuring electrodes 2a, 2b, on the other hand, a detector 4 for measuring voltage is connected to measure the voltage between the first and second electrodes 2a, 2b. The area of the first current-carrying electrode 1a is far smaller than that of the second current-carrying electrode 1b. Therefore, in the living body 5 below the first current-carrying electrode 1a, the current i forms a highly concentrated flow in the depth direction, as shown in FIG. 1B. The second current-carrying electrode 1b, on the other hand, has a large area, so that the current can stably reach the depths of the living body 5, where the current forms a stable flow spreading horizontally to a certain extent. Thus, from the point of view of impedance, the living body 5 can be regarded as being composed of a horizontal part 5b of impedance Zh, extending horizontally, and a vertical part 5c of impedance Zv, extending vertically below the current-carrying electrode 1a, as shown in FIG. 1B.

Inside the living body 5, the above-described flow of current i generates a potential distribution with equipotential lines E illustrated by the broken lines in FIG. 1C. That is, there are some surface points whose potentials are equal to the potentials at some depth-directional positions in the vertical part 5c. In the present case, the measuring electrode 2b is placed at the point P2 on the surface of the living body whose potential is equal to that at the depth-directional position P1. Therefore, with the second measuring electrode 2b, it is possible to measure the potential at the depth-directional point P1. The first measuring electrode 2a, on the other hand, is placed very close to the current-carrying electrode 1a, so that the potential measured with the first measuring electrode 2a can be regarded as equal to the potential at the contact position P3 of the current-caring electrode 1a. As a result, the potential difference measured with the first and second measuring electrodes 2a, 2b can be regarded as equal to the potential difference between the depth-directional ends P1, P3 of the vertical part 5c. Thus, the bioelectrical impedance of the vertical part 5c can be obtained based on the current i supplied by the current source 3 and the voltage detected by the detector 4.

To measure the bioelectrical impedance in the depth direction as described above, the axisymmetrical arrangement of the current-carrying electrodes 1a, 1b and the measuring electrodes 2a, 2b is not always necessary. That is, the distances d between the electrodes need not be the same, and the sizes of the first current-carrying electrode 1a and the first measuring electrode 2a and/or the second current-carrying electrode 2a and the second measuring electrode 2b need not be the same. It should be noted, however, that the configuration may be intentionally made symmetrical as in the above embodiment to obtain the following effects.

Figure 2:
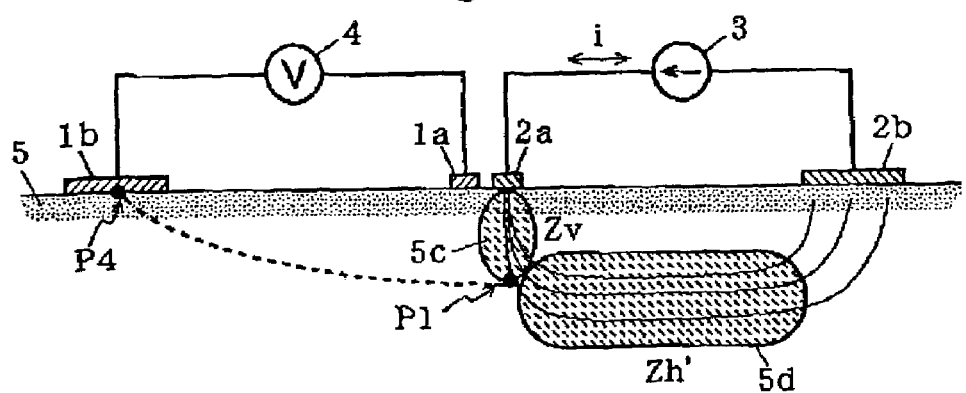
FIG. 2 shows a modification of the measurement method shown in FIG. 1B, where the current source and the detector are transposed.

On the assumption that the internal condition of the living body 5 between the first and second current-carrying electrode 1a, 1b is the same as that between the first and second measuring electrodes 2a, 2b, the measurement result must be the same even when the current source 3 and the detector 4 are transposed as shown in FIG. 2. When the electrode 1a is placed at a point P4, the potential measured with the electrode 1a can be regarded as substantially equal to the potential at the depth-directional point P1. Accordingly, when the above condition is satisfied, the difference in measurement result between the two measurements with the current source 3 and the detector 4 transposed can be regarded as indicative of the measurement error of the bioelectrical impedance Zv. Therefore, it is preferable to calculate the average of the two measurement results and then adopt the average value as the result. Further, when it is possible to determine the reliability of the measurement by a certain method, it is possible to adopt one of the results that is regarded as more reliable.

When the measurement error of the bioelectrical impedance Zv obtained by the measurements with the current source 3 and the detector transposed is small, it can be said that the difference between the two measurement results reflects the difference in the bioelectrical impedance in the horizontal direction inside the living body. That is, it is possible to obtain information about the difference between the bioelectrical impedances Zh, Zh' of the horizontal part 5b in FIG. 1D and the horizontal part 5d in FIG. 2. When, for example, the target of the measurement is the wrist, ankle, spine or another part of the body where the tissue composition below the electrodes changes greatly even with a slight change in the contact positions of the electrodes, it is possible to improve the accuracy of analyzing the target tissue of the measurement by a comparative method including one in which the relative difference in some electrical characteristics, such as volume resistivity, is calculated from the difference between the two measurement results.

EXAMPLES OF MODIFIED MEASUREMENT METHODS

The above-described basic measurement method can be modified in various modes. FIGS. 3–6 show examples with different arrangements of electrodes.

Figure 3:
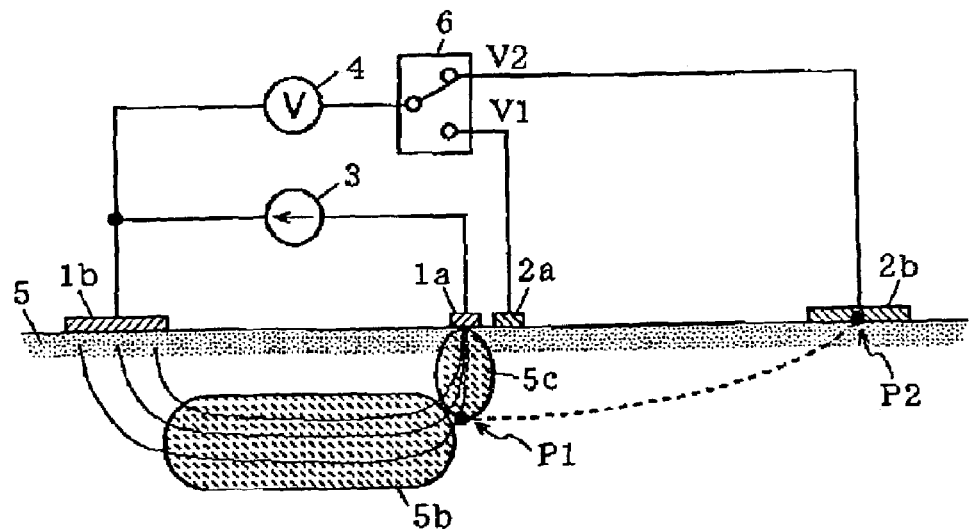
FIG. 3 shows another arrangement of the electrodes in the bioelectrical impedance measurement method according to the present invention.
Figure 4:
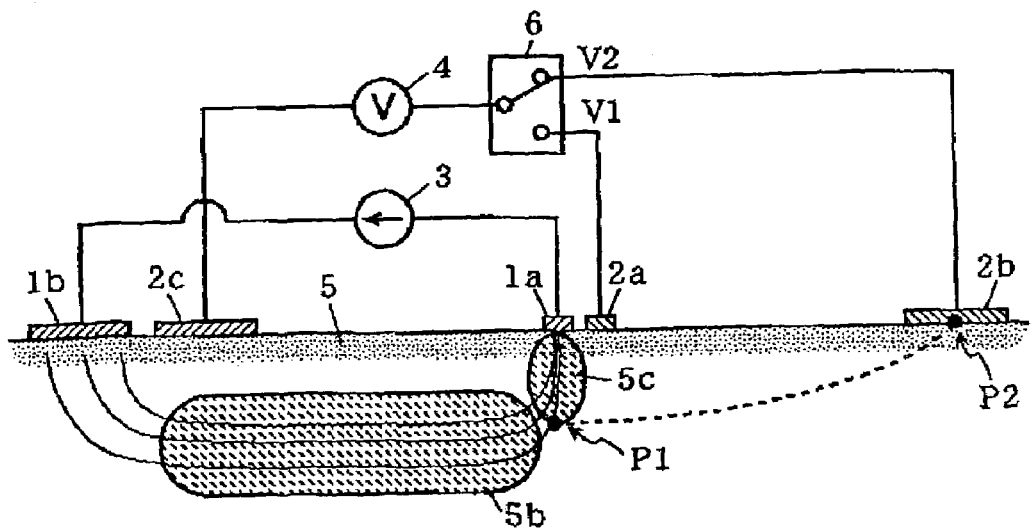
FIG. 4 shows another arrangement of the electrodes in the bioelectrical impedance measurement method according to the present invention.

The two examples shown in FIGS. 3 and 4 use basically the same measurement principle as shown in FIG. 1. By the constitution in FIG. 3, the potential difference between the first and second measuring electrodes 2a, 2b is not directly measured, but the voltage V1 between the second current-carrying electrode 1b and the first measuring electrode 2a, and the voltage V2 between the second current-carrying electrode 1b and the second measuring electrode 2b, are measured by turning the switch 6, and the voltage difference is obtained by calculating V1−V2. It is of course possible to use two detectors corresponding to the measuring electrodes 2a, 2b, respectively, instead of using the switch 6. In the example of FIG. 4, the third measuring electrode 2c is provided away from the second measuring electrode 2b to give a reference potential point for the voltage V1, V2. The third measuring electrode 2c and the second current-carrying electrode 1b may be transposed.

Figure 5:
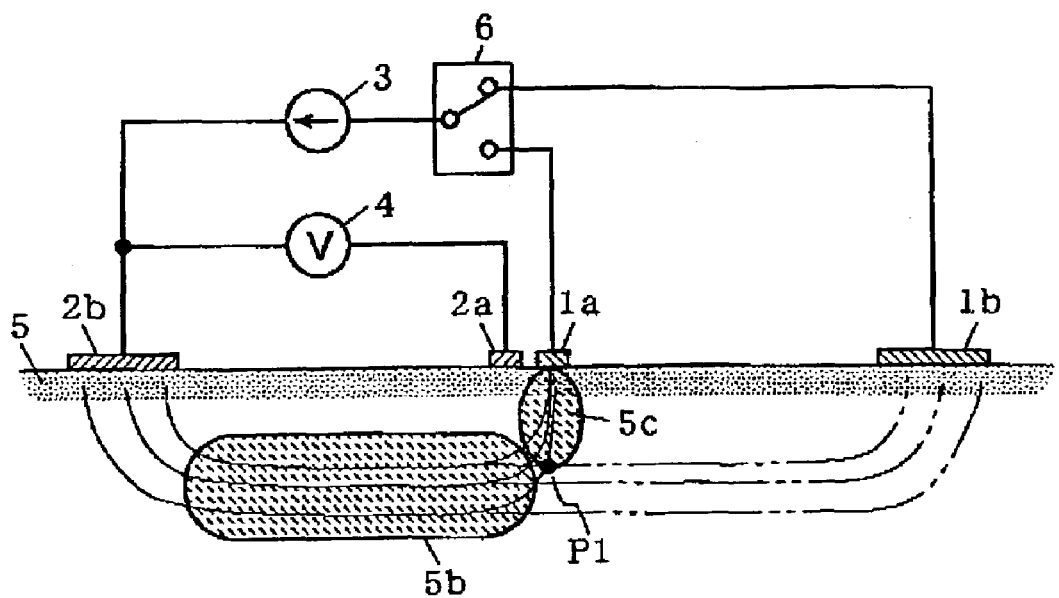
FIG. 5 shows another arrangement of the electrodes in the bioelectrical impedance measurement method according to the present invention.
Figure 6:
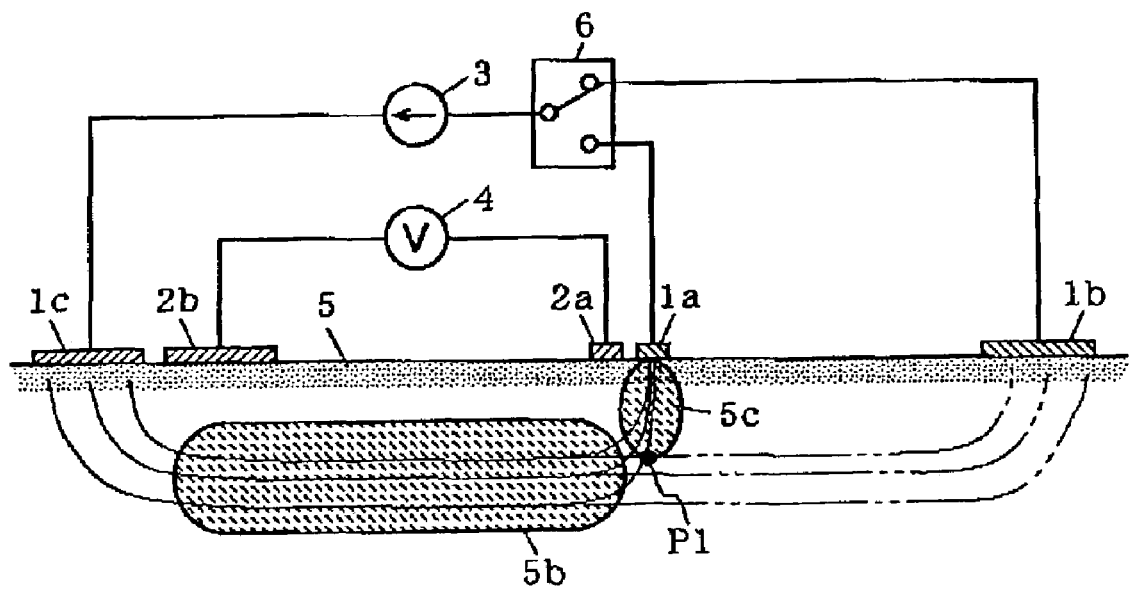
FIG. 6 shows another arrangement of the electrodes in the bioelectrical impedance measurement method according to the present invention.

In the two examples of FIGS. 5, 6, the measurement point of the voltage is not changed as in the examples of FIGS. 3, 4, but the flow path of the radio frequency current i inside the living body 5 is changed, the voltage at the same position is measured for each path, and the difference between the voltages is calculated. The constructions of FIGS. 5 and 6 correspond to those of FIGS. 3 and 4, respectively, with the current source 3 and the detector 4 transposed. The measurement principle, however, is slightly different from the above-described embodiments.

In FIG. 5, when the switch 6 is turned to the lower side to let the current from the current source 3 flow between the first current-carrying electrode 1a and the second measuring electrode 2b, the current path passes through the horizontal part 5b and the vertical part 5c in the living body 5. In this state, the voltage V1 measured with the detector 4 can be regarded as the potential at the contact part of the first current-carrying electrode 1a with respect to the position of the second measuring electrode 2b, because the first measuring electrode 2a is placed very close to the current carrying electrode 1a.

When the switch 6 is turned to the upper side to let the current from the current source 3 flow between the second current-carrying electrode 1b and the second measuring electrode 2b, the current path passes through the horizontal part 5b and another horizontally extending part next to the horizontal part 5b in the living body 5. There, the voltage V2 detected by the detector 4 can be regarded as almost equal to the potential of the lowest part P1 of the vertical part 5c with respect to the position of the second measuring electrode 2b because the current does not pass through the vertical part 5c. Therefore, V1−V2 corresponds to the potential difference between the upper and lower ends of the vertical part 5c. Thus, as in the foregoing examples, it is possible also hereby to obtain the bioelectrical impedance Zv of the vertical part 5c.

As described above, the bioelectrical impedance measurement method according to the present invention can provide information about the inside of the living body in the depth direction below the surface of the living body or deeper than that. Various kinds of information can be obtained, irrespective of the kinds of the living body tissue (fatty tissue, osseous tissue, muscular tissue, blood vessels, etc.). For example, the above-described bioelectrical impedance measurement is applicable to the measurement of the thickness of the subcutaneous fat, as explained below referring to FIG. 7.

Figure 7:
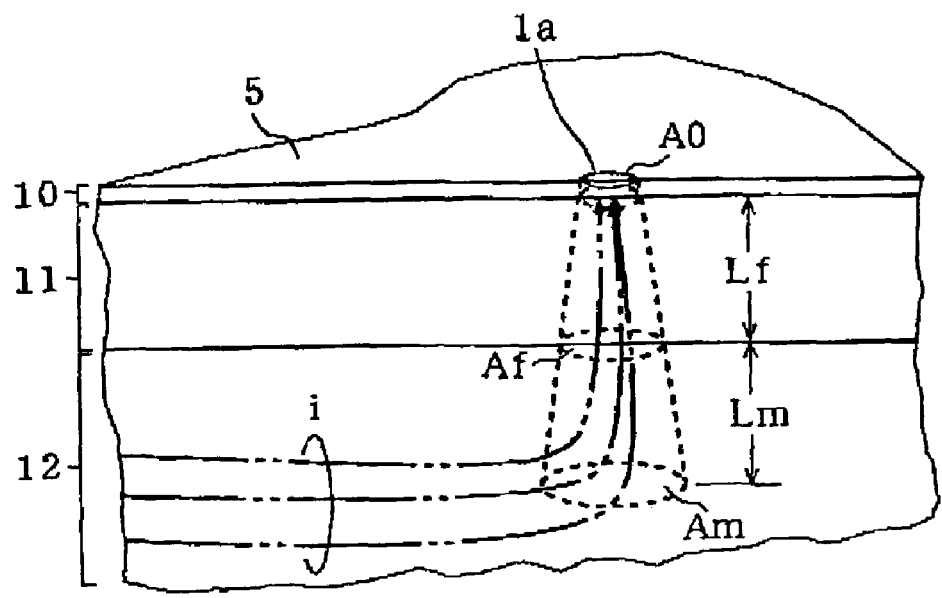
FIG. 7 is a vertical sectional view of a measurement model of the thickness of the subcutaneous fat.

FIG. 7 is a cross-sectional view of the measurement model of the thickness of the subcutaneous fat, showing a cutaneous layer 10, subcutaneous fat 11 thereunder, and muscular tissue layer 12 thereunder. Here, the first current-carrying electrode 1a with a small area is modeled as a cylindrical electrode of area A0. It is assumed that below the first current-carrying electrode 1a, the current path is formed substantially conical, as shown in FIG. 7.

Given the thickness of the subcutaneous fat layer 11 as Lf and the thickness of the part of the muscular tissue layer 12 used as the current path as Lm, the potential difference $\rho V$, which corresponds to the voltage detected by the detector 4 in the case of FIGS. 1A–1C, is given by $$\rho V = i \cdot Zv$$

$$= \rho f \cdot Lf \cdot (i/Af) + \rho m \cdot Lm \cdot (i/Am),$$

where $\rho f$ is the volume resistivity of the subcutaneous fat layer 11 and $\rho m$ is the volume resistivity of the muscular tissue layer 12. Af and Am are the cross-sectional area and the area of the base of the current path, respectively, as shown in FIG. 7. The cross-sectional area is inversely proportional to the second power of the distance from the position of the electrode.

Therefore, $$(1/Af) > (1/Am).$$

It has been known that the fatty layer has the highest volume resistivity of all the tissue layers of the living body, about ten times as high as the volume resistivity of the muscular layer. Therefore, the volume resistivity $\rho f$ of the subcutaneous fat layer 11 and the volume resistivity $\rho m$ of the muscular tissue layer 12 satisfy the following relation:

$$\rho f >> \rho m.$$

Further, if $$Lf \approx Lm.$$

then $$Zv \approx \rho f \cdot Lf/Af,$$

where $\rho f$ is a constant, and Af is uniquely determined by the conditions defined by the size A0 of the first current-carrying electrode, the distance between the current-carrying electrodes, etc. For example, Af≈A0 in the case of approximation by the cylindrical model. Accordingly, Zv is proportional to Lf. Thus, the thickness Lf of the subcutaneous fat layer can be derived from the bioelectrical impedance Zv.

When it is necessary to remove information relating to the cutaneous layer 10, one possible solution is to slightly increase the distance between the first current-carrying electrode 1a and the neighboring first measuring electrode 2a. The reason will be described later.

The thickness of the subcutaneous fat layer is one of the living body information that can be obtained by the present measurement method. In addition, it is possible to get various kinds of information, which will be described later.

The basic idea of the bioelectrical impedance measurement method explained in the above embodiment is to use two current-carrying electrodes as a pair and two measuring electrodes as a pair. In the examples of FIGS. 3-6, the pairs of the electrodes are not apparent. This is, however, because a part of the electrodes is shared or because an additional reference electrode is provided, and the basic idea is to use the pairs of the electrodes. However, it is easy to get to the idea of increasing the number of electrodes to expand the present measurement method. For example, FIG. 1C shows that there is a potential gradient inside the living body 5 as expressed by the equipotential lines E. From this, it is easy to infer that the potentials at different depth-directional positions within the vertical part 5c can be measured by moving from the first measuring electrode 2a to the second measuring electrode 2b on the surface of the living body 5.

Figure 8:
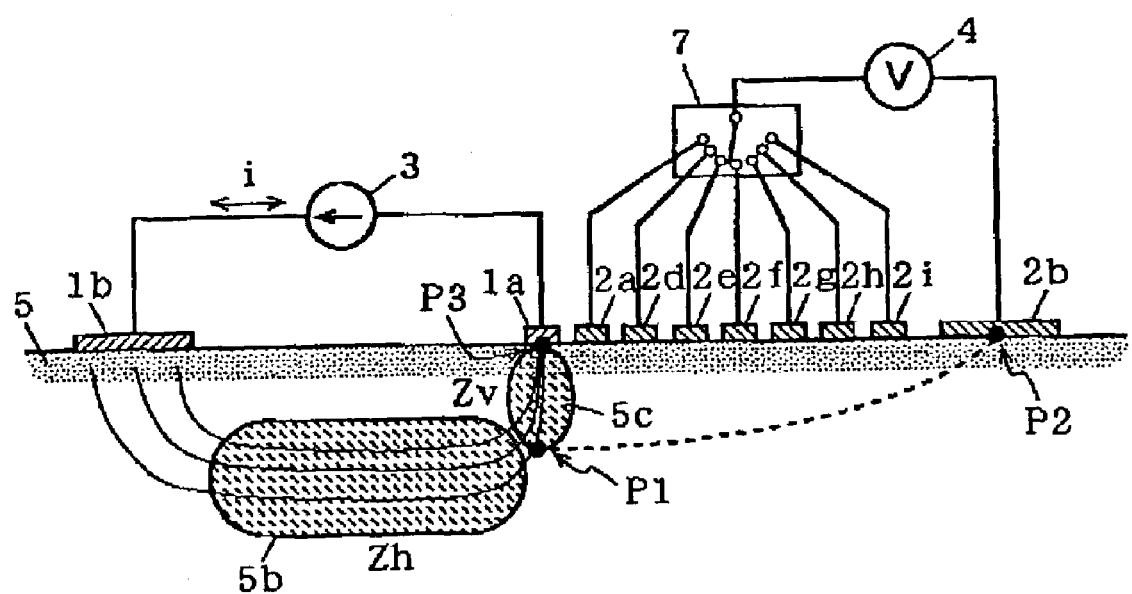
FIG. 8 shows an example of the bioelectrical impedance measurement method according to the present invention, where multiple electrodes are arranged.

FIG. 8 shows an example where multiple measuring electrodes are placed between the first current-carrying electrode 1a and the second measuring electrode 2b. The electrodes 2a, 2d, 2e, 2f, 2g, 2h and 2i are of the same size (e.g. L2×W); the intervals between them need not be the same. While the radio frequency current is supplied between the first and second current-carrying electrodes 1a, 1b, the position of the switch 7 is changed step by step to measure the voltage between the second measuring electrode 2b and each of the electrodes 2a, 2d, 2e, 2f, 2g, 2h and 2i. Thus, not only the total bioelectrical impedance but also a partial bioelectrical impedance of the vertical part 5c can be calculated by taking the difference between the two voltages selected according to necessity. This method provides information about the living body at a particular depth, so that it is possible to obtain accurate information about the muscular tissue layer under the subcutaneous fat, plus information about the blood vessels, etc.

Figure 9:
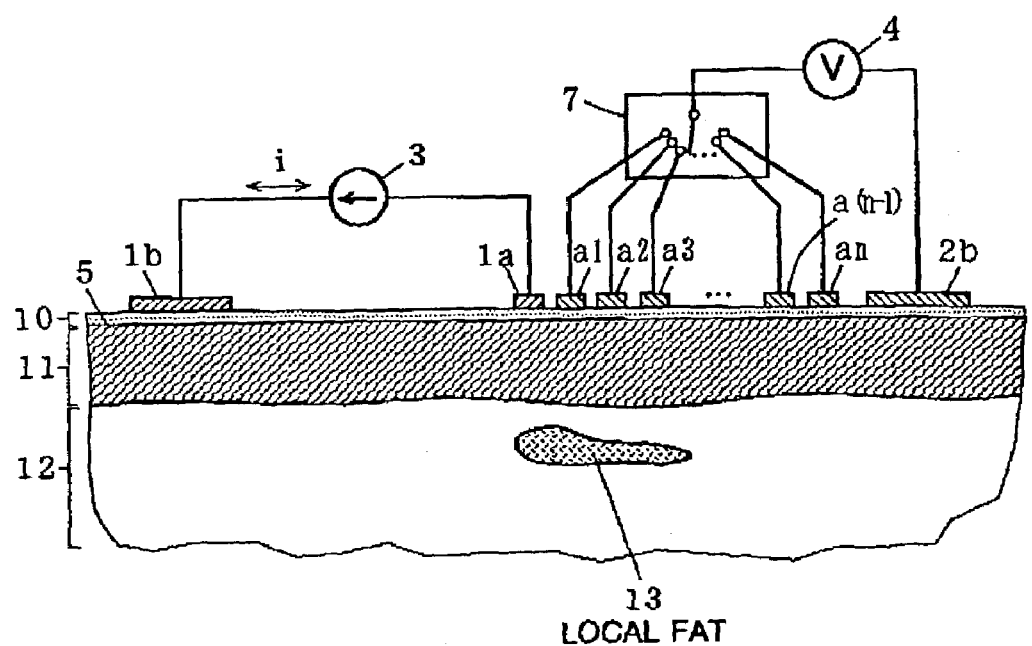
FIG. 9 shows an example of the measurement with the apparatus constructed as shown in FIG. 8.
Figure 10:
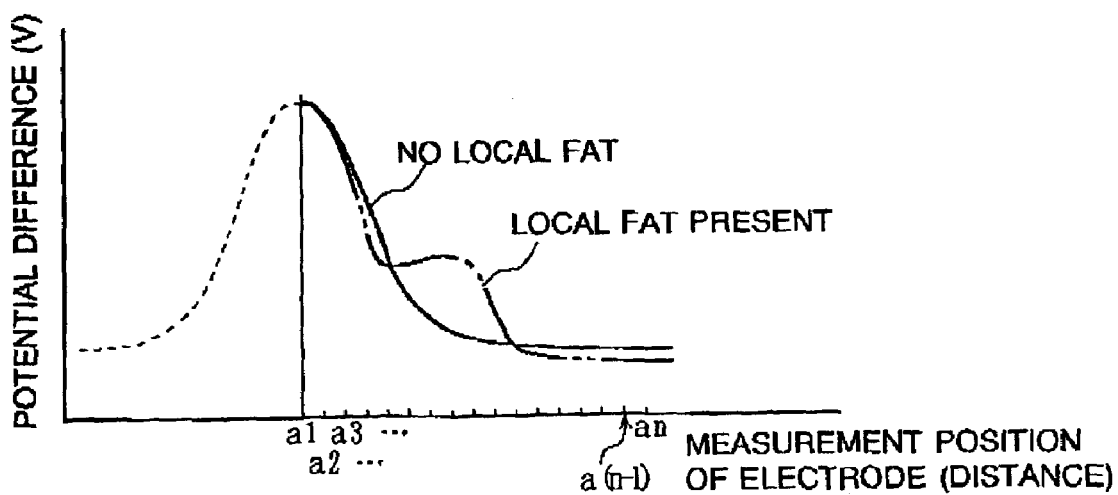
FIG. 10 shows a potential change obtained by an example of the measurement shown in FIG. 9.

An example of the measurement with the multiple electrodes arranged as described above is explained below, referring to FIGS. 9, 10. FIG. 9 shows the case where local fat 13 exists in the muscular tissue layer 12. FIG. 10 shows the distribution of the potential difference obtained by measuring the potentials one after another with n-pieces of the measuring electrodes placed between the first current-carrying electrode 1a and the second measuring electrode 2b, as described above. When local fat 13 exists in the muscular tissue layer 12, the potential distribution in the living body is disturbed because the resistivity of fat is far greater than that of the muscle around it. The result will be as shown FIG. 10. Thus, it is possible to check the existence of the local fat. Further, based on the information about the displacement of the potential difference, it is possible to estimate the size, position and degree of mixture of the local fat.

Figure 11:
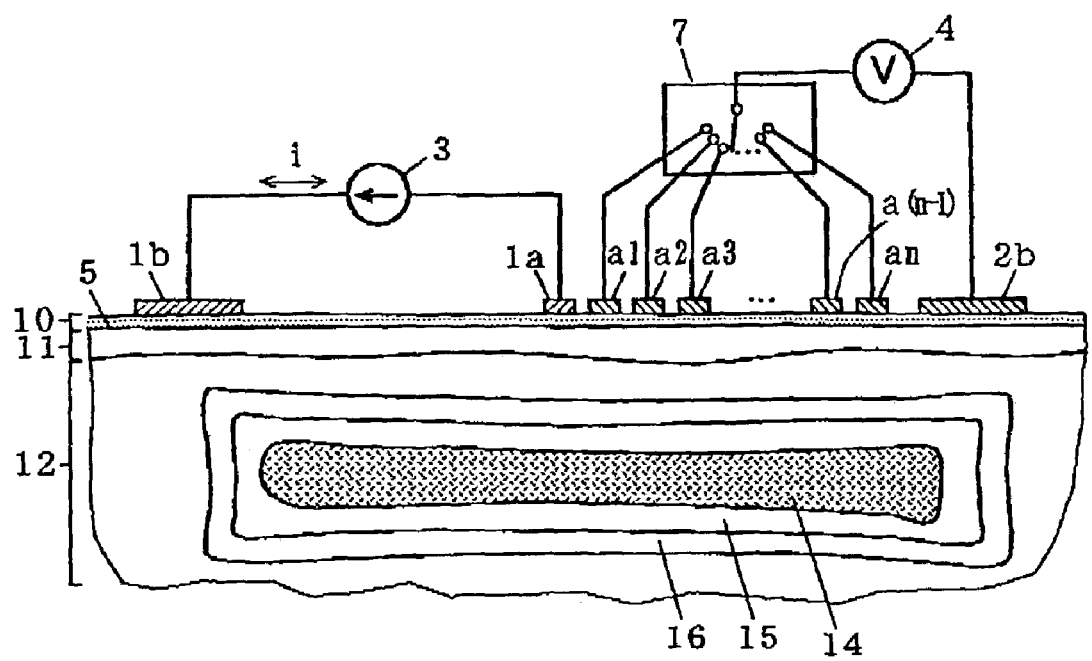
FIG. 11 shows another example of the measurement with the apparatus constructed as shown in FIG. 8.

FIG. 11 shows an example of estimating the balance of the internal structure of the bone by a similar method. As shown in FIG. 11, a bone is composed of a bone marrow tissue 14 surrounded by a cancellous bone 15, which in turn is covered by a cortical bone 16. The volume resistivity of the cortical bone 16 is higher than that of the muscular layer 12 or the cancellous bone 15. Therefore, it is possible to estimate the thickness of the cortical layer 16 based on the potential distribution measured with the electrodes. Also, since the volume resistivity of the cancellous bone 15 is lower than that of the cortical layer 16 or the marrow tissue 14, it is possible to similarly estimate the thickness of the cancellous bone 15 (e.g. degree of growth). Furthermore, in respect to the steatosis of the bone marrow tissue 14 due to aging, it is possible to estimate the progress of the steatosis from the difference in the volume resistivity.

FIG. 8 corresponds to an example where the embodiment of FIGS. 1A–1C is extended to have multiple electrodes. It is naturally possible to extend the embodiments of FIGS. 3–6 to have multiple electrodes so as to obtain accurate information about the living body in the depth direction.

Figure 12:
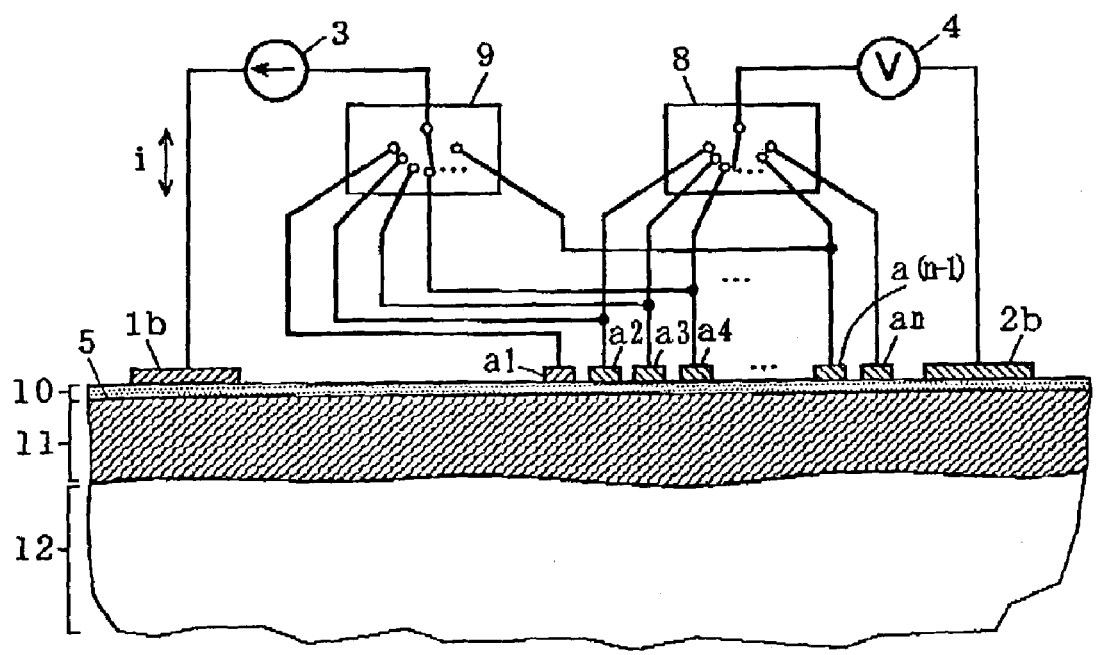
FIG. 12 shows another example of the bioelectrical impedance measurement method according to the present invention where multiple electrodes are arranged.

In arranging the multiple electrodes, it is possible to measure the bioelectrical impedances in the depth direction below different positions on the surface of the living body. FIG. 12 shows an example of such a measurement method. Switch 8 is used to change the connection between the detector 4 and the electrodes, and switch 9 is used to change the connection between the current source 3 and the electrodes.

Figure 13:
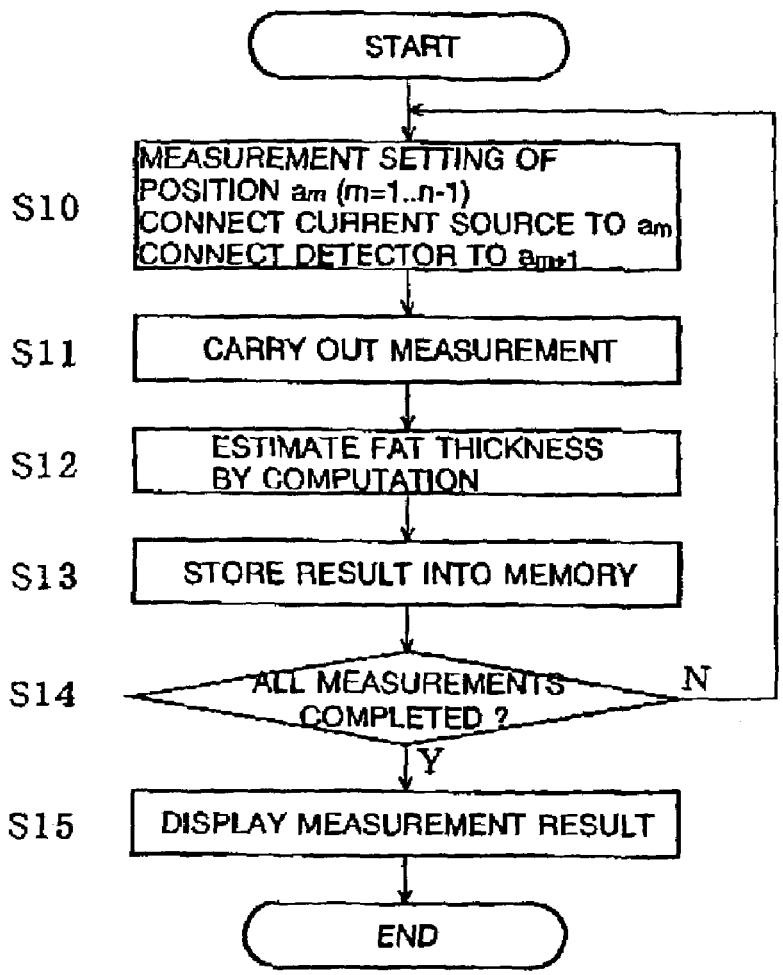
FIG. 13 is a flow chart showing the control process of the measurement by a measurement apparatus with the electrodes constructed as shown in FIG. 12.

FIG. 13 is a flow chart showing a method of controlling the measurement by a measurement apparatus constructed as shown in FIG. 12. After start of a measurement, the parameter m is set m=1, and the switches 8, 9 are operated to connect the current source 3 to the electrode a1 and the detector 4 to the electrode a2 (Step S10). In this state, the current is supplied into the living body to measure the voltage (Step S11). Then, from the measurement result the bioelectrical impedance is calculated, and the fat thickness is estimated based on the bioelectrical impedance (Step S12). The result obtained hereby is the fat thickness below the electrode a1. The result is stored in the memory (Step S13).

Figure 14:
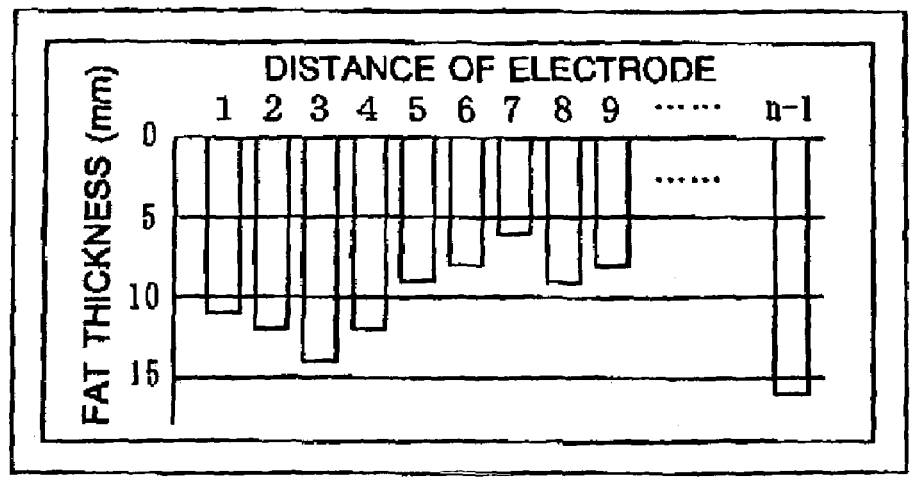
FIG. 14 shows an example of the measurement in FIG. 13.

After that, whether all the measurements are completed or not is determined (Step S14). If not, the process returns to Step S10 to perform the operations of Steps S-S13 after incrementing m by 1. At this time of the operation, the fat thickness below the electrode a2 is estimated, and the result is stored in the memory. Thus, by performing the measurement while shifting both the current-carrying electrode and the measuring electrode one after another, the values of the fat thickness below the electrodes a1–a(n−1) are obtained. After the completion of all the measurements, the process goes from Step S14 to Step S15, where the measurement result is shown on a display or printed with a printer. FIG. 14 shows an example of the output. Thus, with this measurement apparatus, it is easy to obtain the distribution of the fat thickness along a straight line within a given section of the living body.

In the above-described measurement methods, one of the current-carrying electrodes is designed small enough to increase the current density within the living body. If the current density is too low, it is impossible to ensure adequate accuracy of measurement because the signal-to-noise (S/N) ratio of the signal becomes low. If, on the other band, the current density is too high, there is a possibility that the living body tissue is locally damaged by the concentrated current. Thus, there must be an allowable value to be applied to the living body. From the inventor's experiments and experiences, the current density that is satisfactory in regard of safety and S/N ratio is about 1 $\mu A/mm^2$. For example, when the size of the electrode is 3 mm×22 mm, the area of the electrode is 66 $mm^2$, so that the appropriate current is about 66 $\mu A$. The allowable value depends also on the frequency of the radio frequency current. The above allowable value of about 1 $\mu A/mm^2$ corresponds to the frequency of about 50 kHz.

In the above measurements, the electrodes are designed in the form of a rectangular snip. It is obvious that the electrodes are not always required to have that form but may be have different forms, such as a circular or elliptic form. The use of a circular electrode particularly facilitates the theoretical analysis of the electrode, as shown in FIG. 7, and is suitable for measuring a slender object.

[Embodiments of Measurement Apparatus]

It should be easily understood that the bioelectrical impedance measurement method according to the present invention is applicable to various forms or constructions of measurement apparatuses. The following part describes some examples of application.

FIGS. 15A–15B show an electrode pad 20 constructed as a measurement apparatus using the present measurement method, designed to be attached to the subject, where FIG. 15A is a plan view, and FIG. 15B is a sectional view at line B–B' in FIG. 15k. This example is a patch-type electrode pad embodying the measurement method explained using FIGS. 1A–1C.

The base 21 is a thin film sheet made of an insulating material such as polyethylene or polyvinyl chloride. On the base 21, a conductive material such as carbon or silver chloride is deposited to form a terminal part 22 and conductive electrode bases 23, 24, 25, 26 corresponding to the electrodes. On the conductive electrode bases 23, 24, 25, 26, a conductive adhering part 27 made of a gel or conductive rubber is formed, and an insulating adhering part 28 is formed on the part other than the conductive adhering part 27. None of the adhering parts 27, 28 is formed on the terminal part 22; the deposition layer of the conductive material is exposed there. The insulating adhering part 28 is not always required to be adhesive. The adhesiveness securely affixes the electrode pad on the skin of the subject to prevent the pad from being displaced or coming off.

Figure 15:
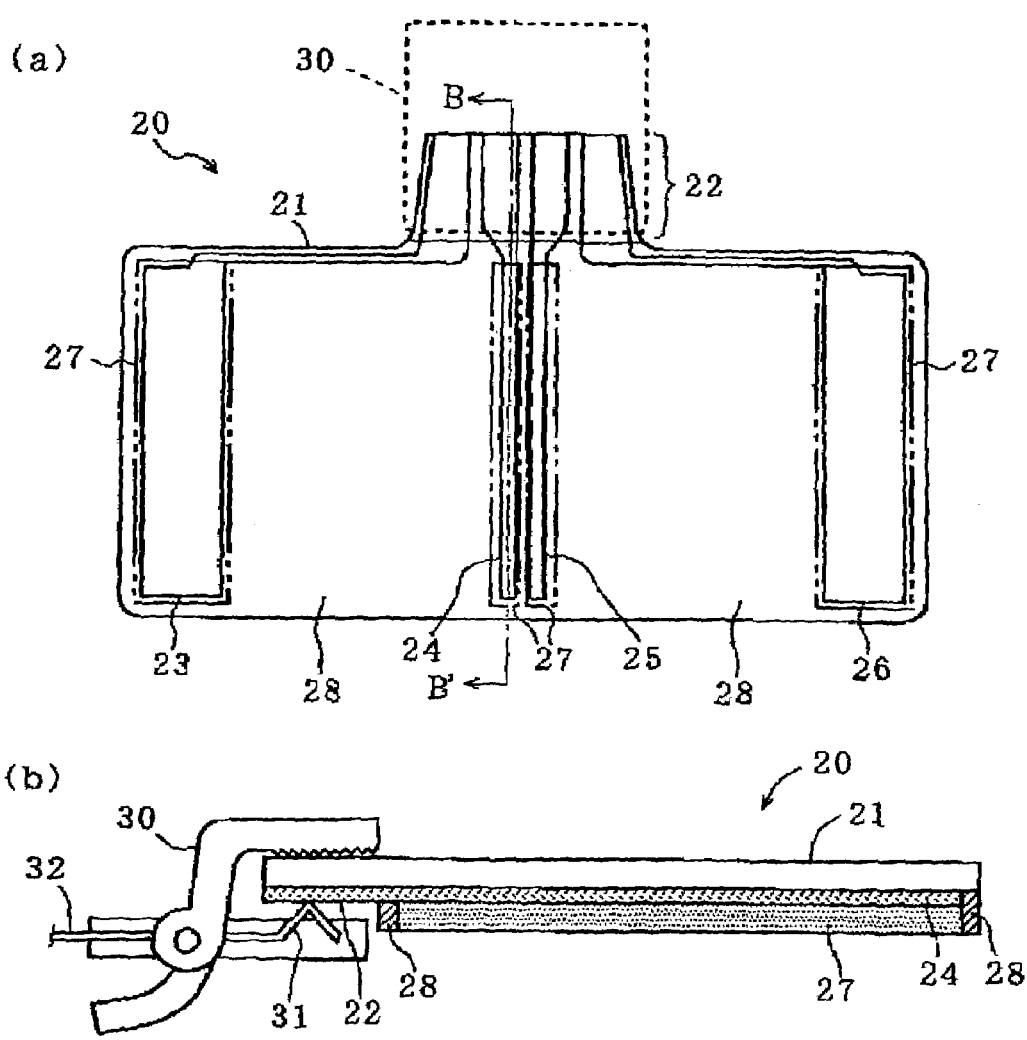
FIGS. 15A–15B show the construction of an electrode pad to be attached to the body of the subject, included in a measurement apparatus using the present measurement method, where
Figure 16:
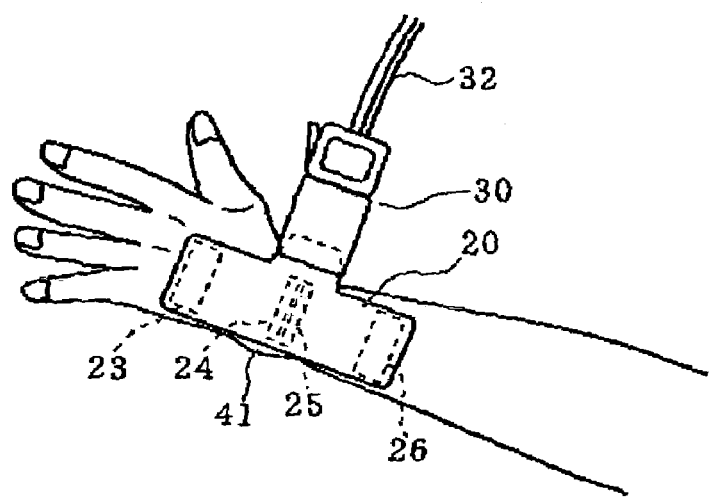
FIG. 16 shows a mode of using the electrode pad shown in FIG. 15.

At the time of use, the electrode 20 is put in contact with the target part of the subject so that the central arrow electrodes 24, 25 are located at the target part. Next, as shown in FIGS. 15B and 16, a clip-like connector 30 is attached by pinching the terminal 22 so that contact plates 31 come in contact with the terminals of the terminal part 22. Then, the cable 32 leading to the contact plates 31 is pulled out. In the example of FIG. 16, the electrode pad 20 is affixed to the joint part of the wrist 41 of the subject. In general the subcutaneous fat layer and the muscular layer at the joint part of the wrist are so thin that the osseous tissue lies immediately below the skin. Therefore, it is convenient to obtain information about the osseous tissue.

At the end of the cable 32 pulled out as described above, the current source 3 and the detector 4 are connected as shown in FIGS. 1A–1C. Ten, supplying weak radio frequency current between the conductive electrode bases 23, 24, the potential difference between the conductive electrode bases 25, 26 is measured, and the bioelectrical impedance is calculated from the current value and the potential difference. Based on the bioelectrical impedance, some information about the living body below the conductive electrode bases 24, 25 can be obtained. For example, it is possible to check the progress of osteoporosis.

Figure 17:
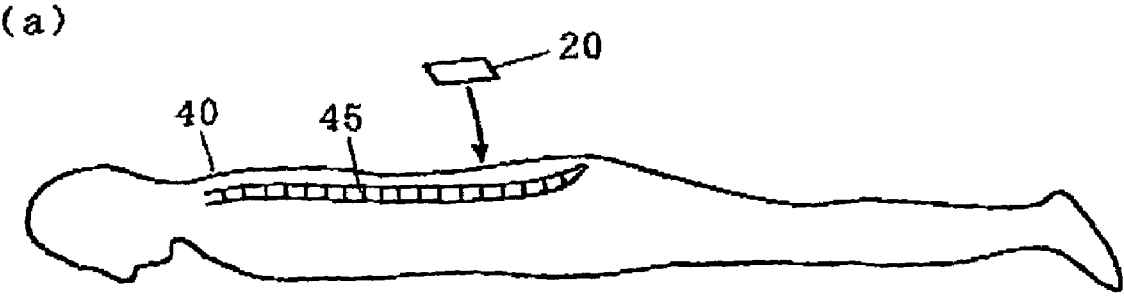
FIG. 17 shows another mode of using the electrode pad shown in FIG. 15.
Figure 17:
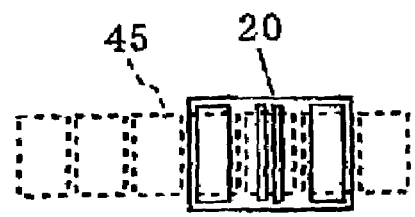

It is of course possible to attach the above-described electrode pad 20 not only to the wrist but also to other parts of the body of the subject to conduct various kinds of measurements. When, for example, information about osseous tissue is desired, it is preferable to select such a part of the living body where the osseous tissue greatly occupies the cross-sectional area of the part, or a part where the osseous tissue lies immediately below the skin. For examples, in addition to the wrist as mentioned above, the ankle and the shank are preferable parts to attach the electrode pad. When the thickness of the subcutaneous fat is to be measured, it is preferable to attach the electrode pad to the brachial, abdomen (especially, flank), etc. When the electrode pad 20 is attached to right above the lumbar vertebrae 45 (strictly speaking, the third and fourth of lumbar vertebrae) as shown in FIG. 17, it is possible to obtain information about the lumbar vertebrae. Further, the electrode pad may be attached to the thigh or other parts where the muscular tissue is well-developed to measure the volume resistivity of the muscular tissue. Then, from the volume resistivity, it is possible to check the progress of the steatosis of the muscular tissue, i.e. a state of muscular tissue with layers of fat inside.

Figure 18:
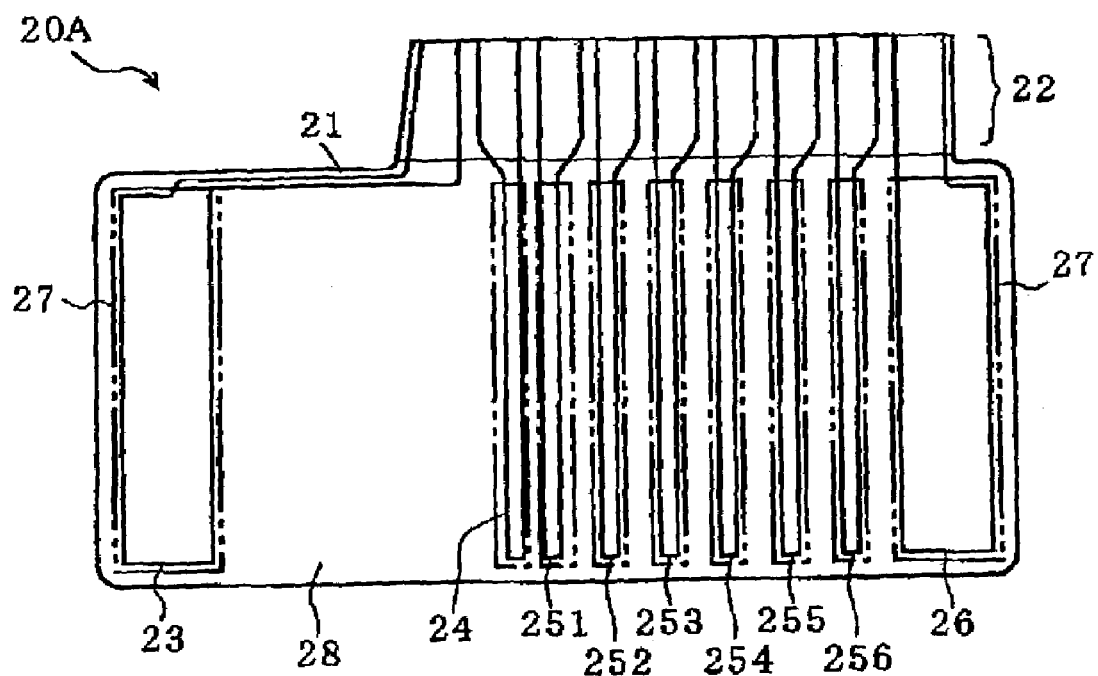
FIG. 18 shows the construction of an electrode pad with the multiple electrodes shown in FIG. 8.
Figure 19:
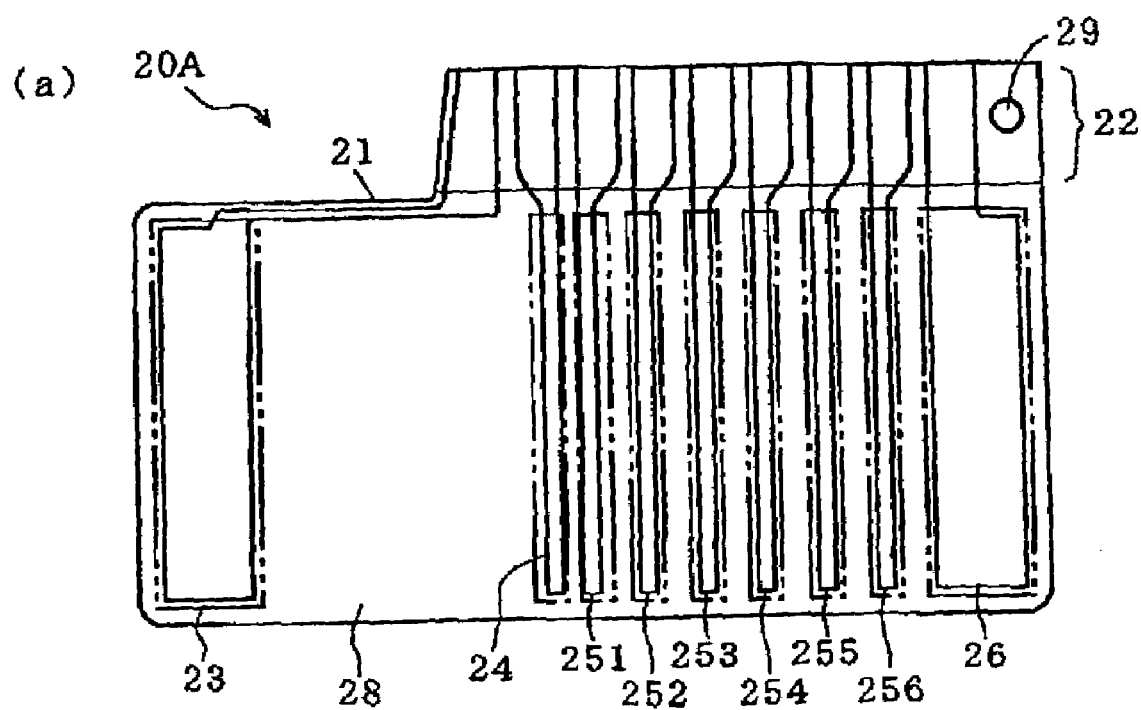
FIGS. 19A–19B show another electrode pad with multiple electrodes.
Figure 19:
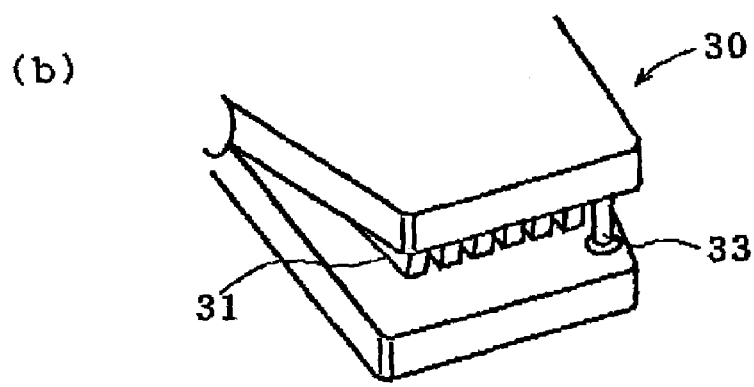

FIGS. 18 and 19A show an example of an electrode pad 20A used in the case of the measurement performed with multiple electrodes arranged like an array, as shown in FIG. 8. The basic structure is the same as shown in FIG. 15; the difference exists in that the conductive electrode base 25 in FIG. 15 is replaced with the multiple conductive electrode bases 251–256 in FIGS. 18 and 19A.

When the terminal 22 has a number of contact points, it is difficult to determine the positions of the contact points by simply pinching the terminal 22 with the clip-type connector from both sides. Taking this into account, the terminal 22 in FIG. 19A has a circular positioning hole 29 formed at its end. The connector 30, on the other hand, has a positioning pin 33, as shown in FIG. 19B. When the connector 30 is attached to the terminal 22 by pinching, the pin 33 is inserted into the bole 29 so that the contact plates 31 and the terminals are positioned to assuredly contact each other. In the case of the construction shown in FIG. 18, it is preferable to make the base 21 of the terminal 22 thicker to increase the strength, and to use such a type of connector that is horizontally inserted into or pulled out like a connector used for the connection of flexible substrates. In this case, it is preferable to provide a come-out prevention mechanism for pressing the connector from both sides with the terminal 22 inserted.

A health management guideline advising apparatus for measuring and displaying the body-fat ratio or other information of the subject is described below as an example of the measurement apparatus using the above-described electrode pad 20.

The health management guideline advising apparatus is a combination of the measurement method according to the present invention, which is suitable for obtaining information of the inside of the living body in the depth direction, and the conventional four-electrode method, which is suitable for obtaining information about the inside of the living body in the horizontal direction, i.e. in the longitudinal direction of the limbs, trunk, etc. This combination makes it possible to carry out such types of measurements that have hitherto been difficult to carry out by conventional methods, and to greatly improve the accuracy of conventional measurements. For example, it is possible to improve the resultant accuracy of measuring the body-fat ratio by carrying out the present measurement method to obtain information relating to the growth of the osseous tissue and the muscular tissue or the degree of aging, and then, using that information, to modify the parameters used for estimating the body-fat ratio from the measurement result obtained by the conventional four-electrode method. It is also possible to measure the thickness of the subcutaneous fat of each part of the body and feed the results back to the estimation of the body fat by ale conventional method to improve the accuracy.

Figure 20:
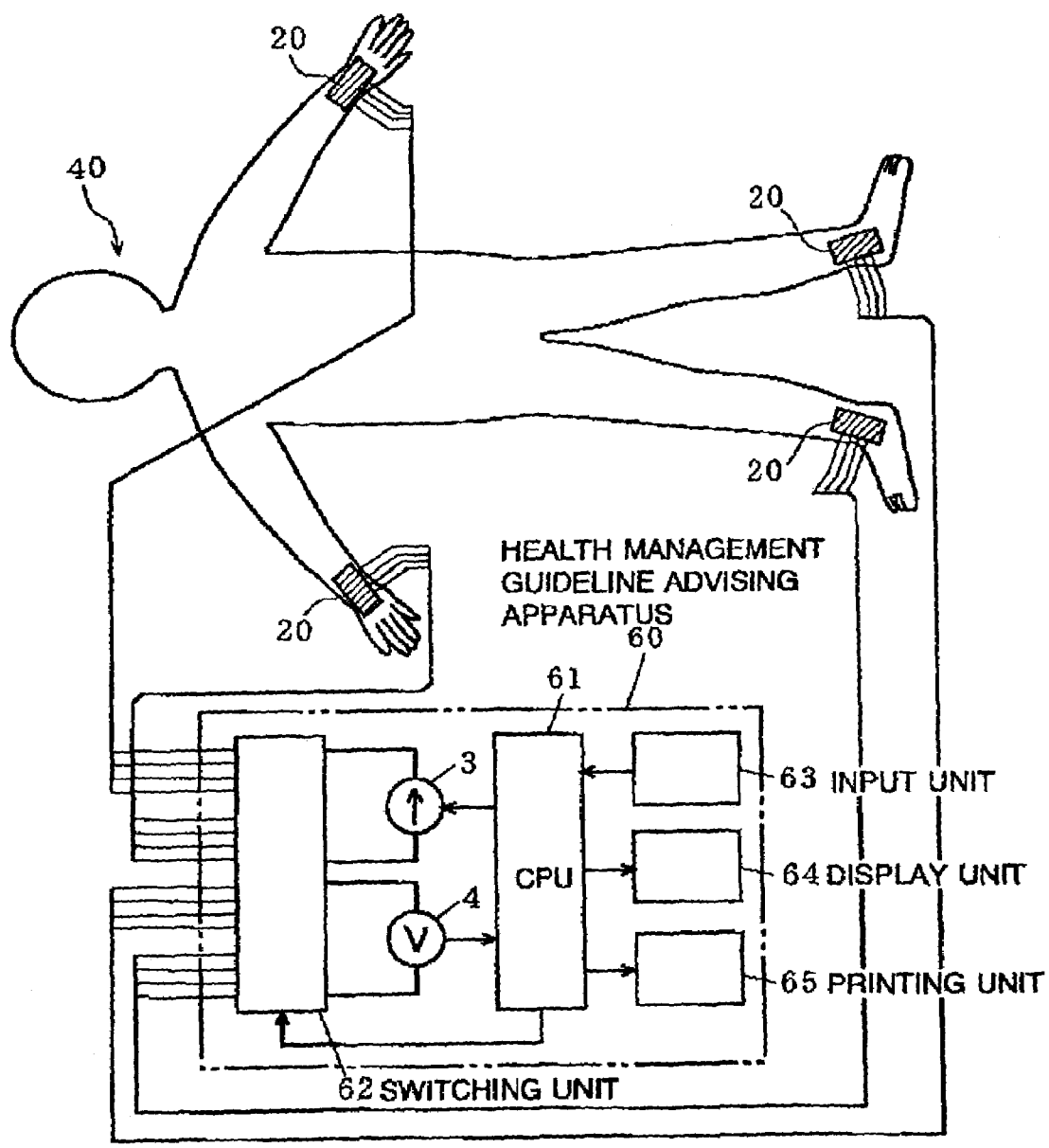
FIG. 20 shows an example of the measurement by a health management guideline advising apparatus using a bioelectrical impedance measurement apparatus according to the present invention.

FIG. 20 shows an example of the body composition measurement using the present health management guideline advising apparatus. The subject 40 lies in a supine position on the bed, bare-footed, legs slightly open, and arms slightly away from the trunk. To the wrists and ankles of the subject 40, the electrode pads 20 having the above-described two pairs of the electrodes are affixed. The four cables pulled out from the electrode pads 20 are connected to the health management guideline advising apparatus 60. The health management guideline advising apparatus 60 includes: a central processing unit (CPU) 61 as the main unit for performing various computations and controls; a switching unit 62 having plural switches inside; a current source 3 and a detector 4 both connected to the switching unit 62; an input unit 63 having keys, switches and other parts; a display unit 64 capable of displaying character information, image information, etc.; and a printing unit 65 for printing the measurement result and/or other information.

Figure 21:
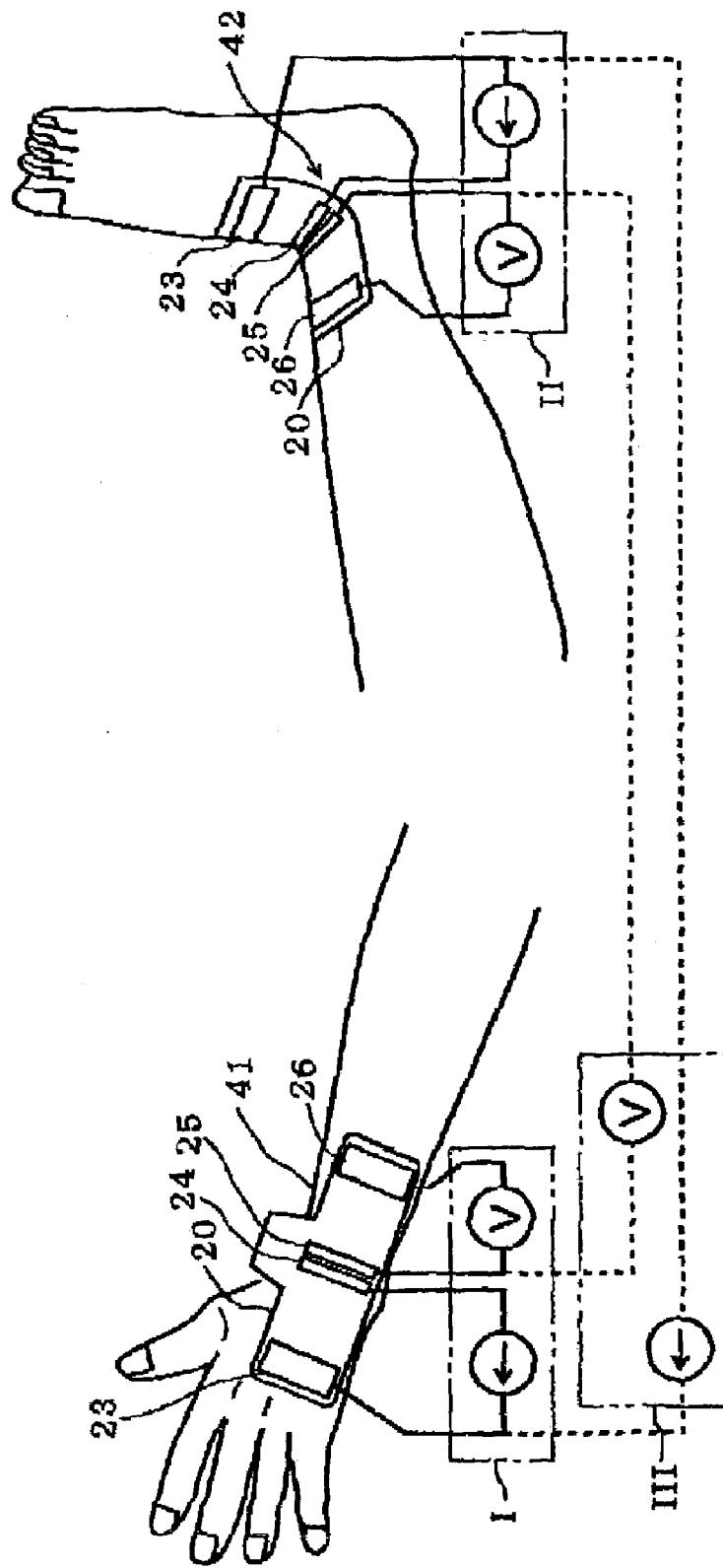
FIG. 21 is a drawing for explaining the operation of the health management guideline advising apparatus shown in FIG. 20.

The above construction enables the following measurement. When, as denoted by "I" in FIG. 21, the switching unit 62 is controlled so that the current source 3 is connected to the electrodes 23, 24 of the electrode pad 20 affixed to the wrist 41 and the detector 4 is connected to the electrode 25, 26, the CPU 61 can calculate the bioelectrical impedance in the depth direction of the wrist 41. When, as denoted by "II", the switching unit 62 is controlled so that the current source 3 is connected to the electrodes 23, 24 of the electrode pad 20 affixed to the ankle 42 and the detector 4 is connected to the electrode 25, 26 the CPU 61 can calculate the bioelectrical impedance in the depth direction of the ankle 42. The same argument holds also in the case of the wrist or ankle on the other side.

When, as denoted by "III", the current source 3 is connected to the electrode 23 of the electrode pad 20 affixed to the wrist 41 and the electrode 23 of the electrode pad 20 abed to the ankle 42 and the electrode 4 is connected to the electrode 25 of the electrode pad 20 affixed to the wrist 41 and the electrode 25 of the electrode pad 20 affixed to the ankle 42, it is possible to supply the current between the wrist and the ankle to measure the potential difference between the wrist and the ankle through almost the entire part of the arm, trunk and leg, using the electrodes placed inside. That is, it is possible to cry out the bioelectrical impedance measurement by the conventional four-electrode method.

According to a preinstalled control program, the CPU 61 controls the switching unit 62 to change the destination to connect the current source 3 and the detector 4 as described above, for example. For every switching operation, the CPU 61 supplies a preset magnitude of current into the body of the subject 40 by controlling the current source 3, and reads the voltage value obtained by the detector 4 at that moment. Then, based on the bioelectrical impedance obtained by one or more operation modes, the CPU 61 calculates the body-fat ratio or other values according to a preset algorithm, and displays the values on the display unit 64 or, when requested, prints the values by the printing unit 65. Thus, by attaching the electrode pads 20 capable of realizing the present measurement method to the wrist and the ankle of the subject, not only the present measurement method is realized but also the conventional method of measuring the bioelectrical impedance can be carried out without problem.

Figure 22:
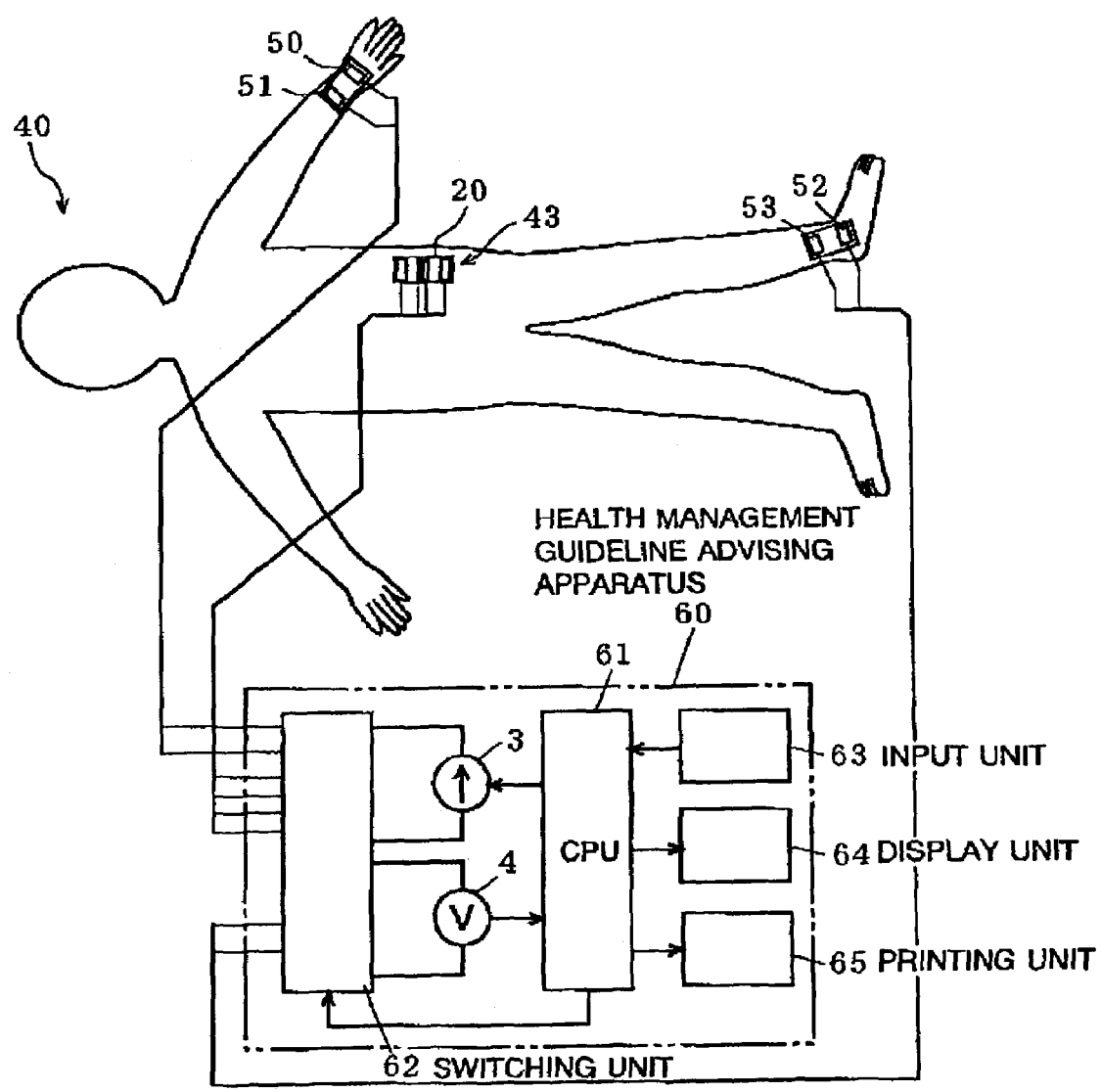
FIG. 22 shows another example of the measurement by a health management guideline advising apparatus using a bioelectrical impedance measurement apparatus according to the present invention.

FIG. 22 shows an example of the body composition measurement using another health management guideline advising apparatus. In this example, an electrode pad having the above-described two electrodes 50 and 51, or 52 and 53, is affixed to each wrist and ankle on one side of the subject 40, and the electrode pad 20 used by the present measurement method is affixed to the abdomen 43. That is, the four electrodes 50, 51, 52, 53 are used to measure the bioelectrical impedance between the wrist and the ankle by the conventional four-electrode method.

Figure 23:
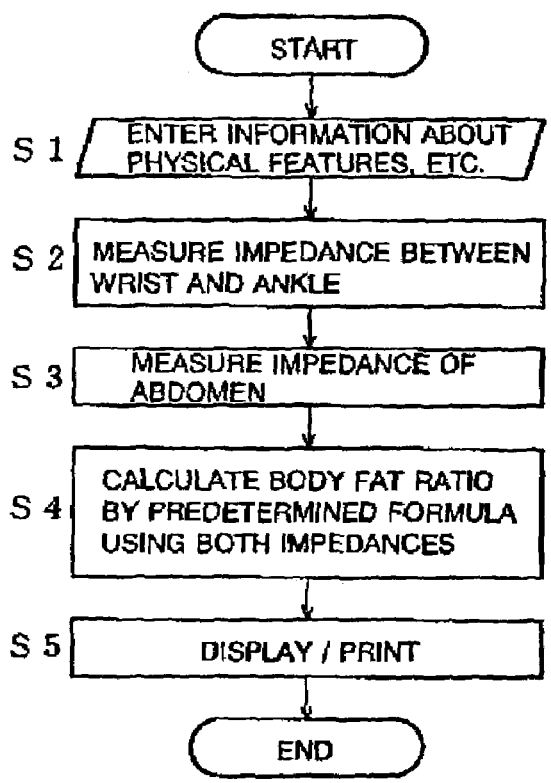
FIG. 23 is a flow chart showing the measurement operation of the heath management guideline advising apparatus shown in FIG. 22.

The operation of measuring the body-fat ratio by the present health management guideline advising apparatus is explained referring to the flow chart shown in FIG. 23. First, the fundamental parameters for the calculation of the body fat, such as the height, weight, age, sex or other attributes of the subject, are entered through the input unit 63 (Step S1). When, for example, a measurement start key is operated to start the actual measurement, the switching unit 62 connects the current source 3 between the electrodes 50, 52, and the detector 4 between the inner electrodes 51, 53. With this configuration, the bioelectrical impedance between the wrist and the ankle is measured by the conventional four-electrode method (Step S2).

Next, the switching unit 62 connects the current source 3 between a pair of current-carrying electrodes and the detector 4 between a pair of measuring electrodes. With this configuration, the biological impedance of the abdomen in the depth direction is measured (Step S3). This reflects the thickness of the subcutaneous fat below the electrode pad 20. The CPU 61 calculates the body-fat ratio, using the two impedance values measured and based on the formula (or algorism) according to the fundamental parameters entered at the beginning (Step S4). The result is displayed on the display unit 64 or printed by the printing unit 65 (Step S5). By such a construction, the accuracy of calculating the body-fat ratio is greatly improved because the thickness of the subcutaneous fat in the abdomen of the subject is known beforehand with considerable accuracy.

Figure 24:
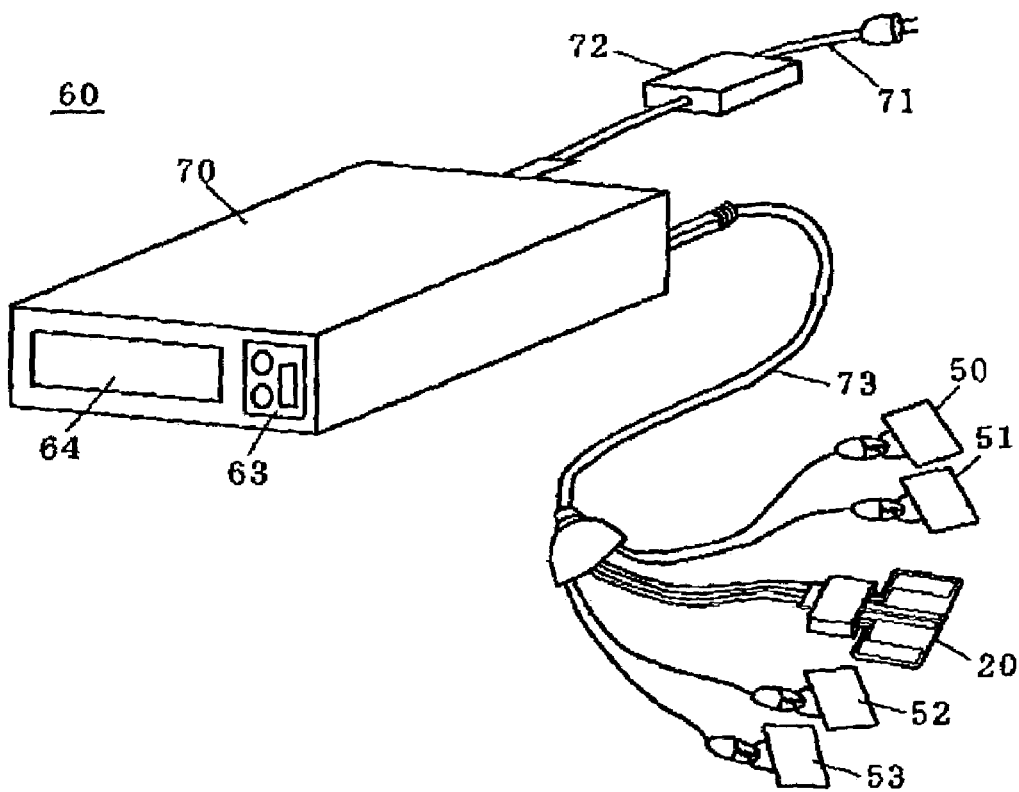
FIG. 24 is an outline view of the health management guideline advising apparatus shown in FIG. 22.

FIG. 24 is an outline view of al example of the above health management guideline advising apparatus. The main body 70 has the input unit 63 and the display unit 64 at its front, and a power cord 71 with an AC adapter 72 and an electrode cable 73 are pulled out from the back. At the ends of the electrode cable 73, the above-described electrode pads 20 and the electrodes 50, 51, 52, 53 are provided and are removable.

As explained above, the bioelectrical impedance measurement method according to the present invention can provide adequately meaningful, significant information about a living body even when independently applied to a measurement apparatus. Further, the combination of the above method with the conventional four-electrode method or another measurement method is very effective in obtaining such information about the living body that has hitherto been difficult to measure, or in improving the accuracy of information obtained by conventional measurement methods.

Figure 25:
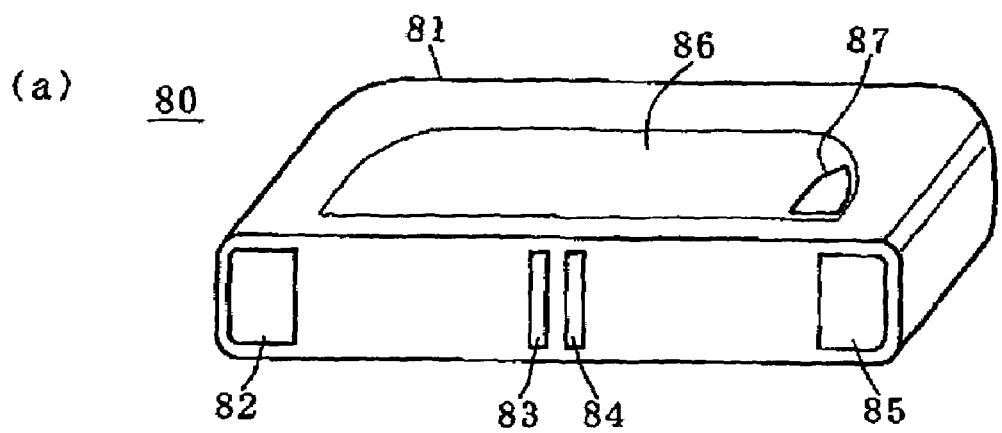
FIGS. 25A–25B are outline views of an example of a portable health management guideline advising apparatus according to the present invention.
Figure 25:
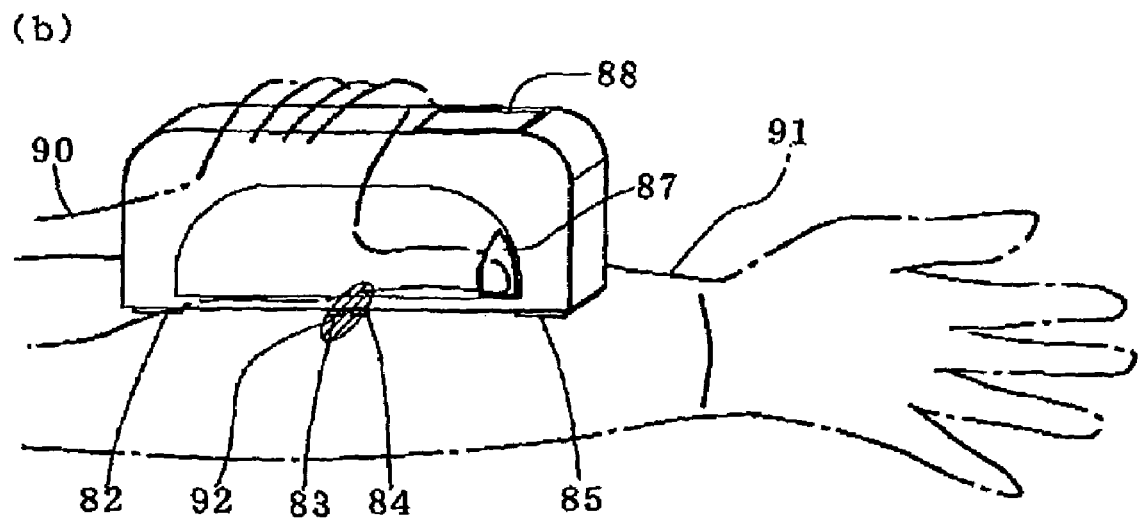

The above-described health management guideline advising apparatus is a relatively large one. For the purpose of measuring the thickness of subcutaneous fat or the like, a smaller, easy-to-handle apparatus is desirable. FIGS. 25A–25B show an example of a portable health management guideline advising apparatus 80, where FIG. 25A is an outline view of the apparatus 80 observed from the bottom side, and FIG. 25B shows the apparatus 80 in use. In this apparatus 80, the main body and the electrodes are integrally constructed; four electrodes, i.e. a pair of current-carrying electrodes 82, 83 and a pair of measuring electrodes 84, 85, are arranged on the bottom of the box-shaped flat body 81, each electrode slightly projecting from the bottom. The electrodes 82, 83, 84, 85 are made of such metal as stainless steel or silver chloride. On one side of the body 81, a slip-prevention member 86 is fixed to make the body 81 less able to slip when held, a part of which is a measurement start key 87 that serves also as the power switch. A display part 88 for showing the measurement result is provided at the top of the body 81.

At the time of use, the examiner 90 holds the portable health management guideline advising apparatus 80 as shown in FIG. 25B, and presses the electrodes 82–85 on the body of the subject 91. There, the target part 92 shall be located below the central electrodes 83, 84. Since the electrodes 82–85 project slightly from the bottom of the machine body 81, the electrodes 82–85 securely contact the surface of the skin of the subject 91. Thus, maintaining the adequate contact pressure, the measurement can be stably carried out. Also, while pressing the apparatus 80 on the target part 92 of the subject 91, the examiner 90 can operate the measurement start key 87, so that the measurement ran be carried out in a stable and simple manner.

Figure 26:
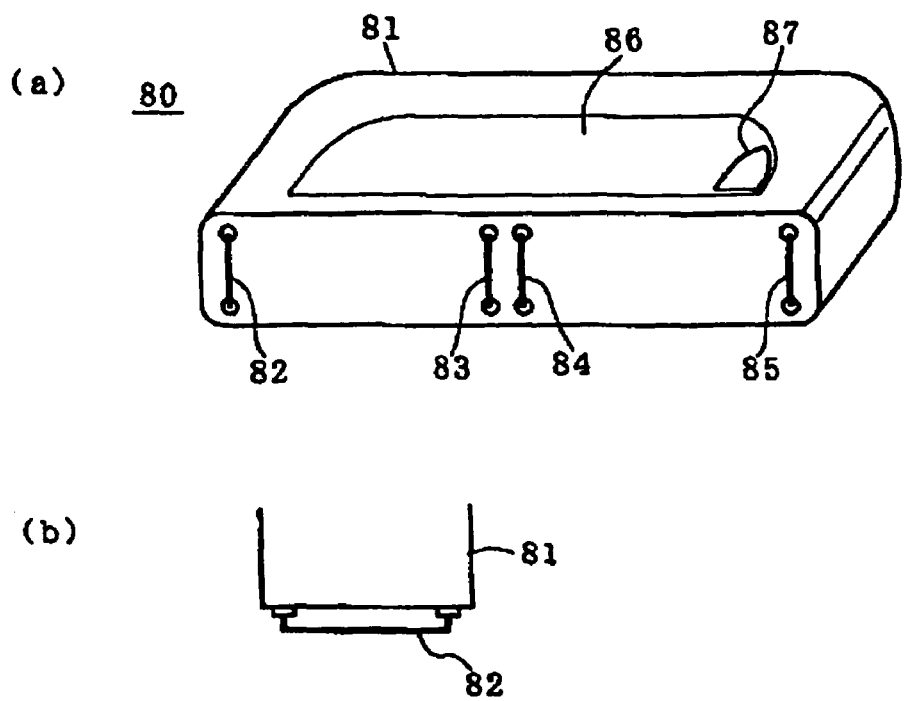
FIGS. 26A–26B are outline views of another portable health management guideline advising apparatus according to the present invention.
Figure 27:
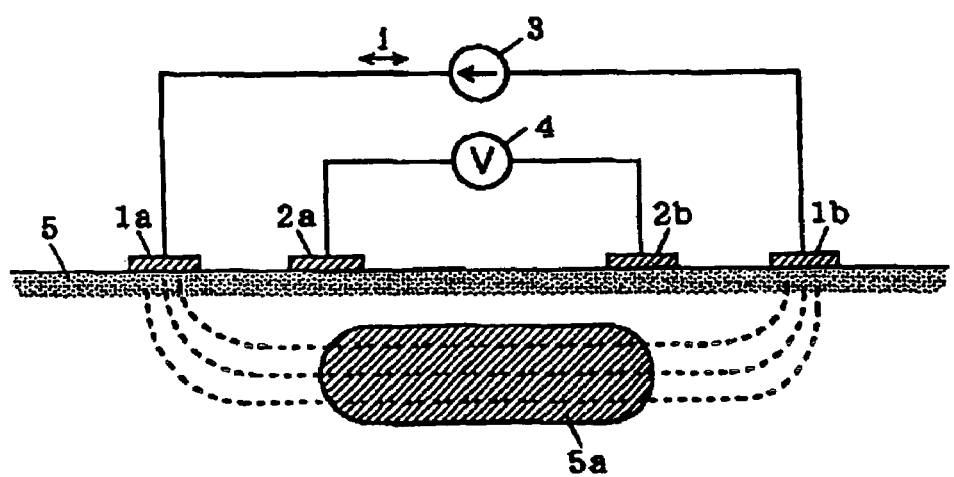
FIG. 27 is a sectional view showing the principle of a conventional bioelectrical impedance measurement method using the four-electrode method.

FIGS. 26A–26B show another example of the portable health management guideline advising apparatus 80, which differs from the apparatus shown in FIG. 25A in respect of the form of the electrodes. FIG. 26A is an outline view of the apparatus 80 observed from the bottom side, and FIG. 26B is a side view of the bottom part of the apparatus 80. In this example, the electrodes 82–85 are U-shaped wires projecting from the bottom face of the body 81. By pressing this apparatus on the body surface of the subject the contact pressure can be maintained high, whereas the contact area is small. Thus, the measurement can be carried out stably and accurately.

It should be noted that any of the above embodiments is a mere example and can be further changed or modified within the spirit and scope of the present invention.

The invention claimed is:

1. A bioelectrical impedance measurement method for measuring bioelectrical impedance relating to information about an inside of a limited part of a living body from an electrical signal measured on a substantially flat surface of the living body, having:

a first measurement mode where a set of current-carrying electrodes including a first electrode and a second electrode for being attached to the surface of the living body set apart from each other at predetermined distances to generate a flow of radio frequency current in the living body between the first electrode and the second electrode, the first electrode having a smaller contact area than the second electrode; and a second measurement mode where a flow of radio frequency current is generated between the second electrode and a third electrode for being attached to the surface of the living body on an extension of a straight line drawn between the first electrode and the second electrode, where the extension is made beyond the first electrode, and the method comprising:

measuring a voltage on the surface of the living body between a part adjacent to the first electrode and a contact part of the second electrode for each of the first and second measurement modes, and calculating a voltage difference between the two modes; and calculating the bioelectrical impedance in a depth direction below a contact part of the first electrode, based on the voltage difference and a value of the radio frequency current.

2. A bioelectrical impedance measurement apparatus for measuring a bioelectrical impedance relating to information about an inside of a limited part of a living body from an electrical signal measured on a substantially flat surface of the living body, which includes:

a) a set of current-carrying electrodes to be attached to the surface of the living body set apart from each other by predetermined distances, including a first current-carrying electrode, a second current-carrying electrode, and a third current-carrying electrode for being attached to the surface of the living body on an extension of a straight line drawn between the first current-carrying electrode and the second electrode, where the extension is made beyond the first current-carrying electrode, the first current-carrying electrode having a smaller contact area than the second current-carrying electrode and generating high density current flow in a depth direction below a contact part of the first current-carrying electrode;

b) a radio frequency current supplying means for generating a flow of radio frequency current in the living body between the first current-carrying electrode and the second current-carrying electrode in a first measurement mode, and for generating a flow of radio frequency current in the living body between the second current-carrying electrode and the third current-carrying electrode in a second measurement mode;

c) measuring electrodes including a first measuring electrode for being attached adjacent to the first current-carrying electrode on the surface of the living body, and a second measuring electrode for being attached adjacent to the second current-carrying electrode;

d) a voltage measuring means for measuring a voltage between the first measuring electrode and the second measuring electrode for each of the first and second measurement modes, and for calculating a voltage difference between the two modes; and e) a calculating means for calculating the bioelectrical impedance in a depth direction below a contact part of the first current-carrying electrode, based on the voltage difference and a value of the radio frequency current.

3. The bioelectrical impedance measurement apparatus according to claim 2, wherein the current-carrying electrodes and the measuring electrodes are adapted to be linearly arranged on the surface of the living body.

4. The bioelectrical impedance measurement apparatus according to claim 2, wherein one or more additional measuring electrodes are arranged between the first measuring electrode and the second measuring electrode, and voltages between these electrodes are measured to measure the bioelectrical impedances of regions at different positions in the depth direction below or nearly below the contact part of the first current-carrying electrode.

5. The bioelectrical impedance measurement apparatus according to claim 2, wherein the current-carrying electrodes and the measuring electrodes are formed on one side of a sheet-like member, and the sheet-like member is configured to be affixed to the surface of the living body to perform a measurement.

6. A bioelectrical impedance measurement method for measuring a bioelectrical impedance relating to information about an inside of a limited part of a living body from an electrical signal measured on a substantially flat surface of the living body, comprising:

attaching a set of current-carrying electrodes including a first current-carrying electrode and a second current-carrying electrode to the surface of the living body set apart from each other by predetermined distances to generate a flow of radio frequency current inside the living body, the first current-carrying electrode having a smaller contact area than the second current-carrying electrode and generating high density current flow in a depth direction below a contact part of the first current-carrying electrode;

measuring a potential difference generated with the radio frequency current between a first part adjacent to the first current-carrying electrode on the surface of the living body and a second part away from the first part by a distance equal to or greater than a preset distance; and calculating the bioelectrical impedance in a depth direction below a contact part of the first current-carrying electrode, based on the potential difference and a value of the radio frequency current, wherein measuring the potential difference includes obtaining a voltage between a first measuring electrode for being attached to the first part and a second measuring electrode for being attached to the second part on the surface of the living body, the method further comprising:

linearly arranging the first and second current-carrying electrodes and the first and second measuring electrodes on the surface of the living body;

placing the first measuring electrode adjacent to the first current-carrying electrode on an extension of a straight line drawn between the first current-carrying electrode and the second current-carrying electrode;

placing the second measuring electrode away from the first measuring electrode at a distance equal to the distance between the first current-carrying electrode and the second current-carrying electrode;

performing a first measurement for measuring a voltage between the first measuring electrode and the second measuring electrode while supplying a current into the living body through the first current-carrying electrode and the second current-carrying electrode;

performing a second measurement for measuring a voltage between the first current-carrying electrode and the second current-carrying electrode while supplying a current into the living body through the first measuring electrode and the second measuring electrode; and calculating the bioelectrical impedance in the depth direction below the first current-carrying electrode, and below the first measuring electrode by using results of the first measurement and the second measurement.

7. A bioelectrical impedance measurement method for measuring a bioelectrical impedance relating to information about an inside of a limited part of a living body from an electrical signal measured on a substantially flat surface of the living body, comprising:

attaching a set of current-carrying electrodes including a first current-carrying electrode and a second current-carrying electrode to the surface of the living body set apart from each other by predetermined distances to generate a flow of radio frequency current inside the living body, the first current-carrying electrode having a smaller contact area than the second current-carrying electrode and generating high density current flow in a depth direction below a contact part of the first current-carrying electrode;

measuring a potential difference generated with the radio frequency current between a first part adjacent to the first current-carrying electrode on the surface of the living body and a second part away from the first part by a distance equal to or greater than a preset distance; and calculating the bioelectrical impedance in a depth direction below a contact part of the first current-carrying electrode, based on the potential difference and a value of the radio frequency current, wherein measuring the potential difference includes obtaining a voltage between a first measuring electrode for being attached to the first part and a second measuring electrode for being attached to the second part on the surface of the living body, the method further comprising:

arranging the first and second current-carrying electrodes and the first and second measuring electrodes rectilinearly on the surface of the living body;

placing the first measuring electrode adjacent to the first current-carrying electrode on an extension of a straight line drawn between the first current-carrying electrode and the second current-carrying electrode;

placing the second measuring electrode away from the first measuring electrode by a distance equal to a distance between the first current-carrying electrode and the second current-carrying electrode;

performing a first measurement for measuring a voltage between the first measuring electrode and the second measuring electrode while supplying a current into the living body through the first current-carrying electrode and the second current-carrying electrode;

performing a second measurement for measuring a voltage between the first current-carrying electrode and the second current-carrying electrode while supplying a current into the living body through the first measuring electrode and the second measuring electrode; and calculating a difference between the bioelectrical impedances in a horizontal direction at a depth below or nearly below and between the first current-carrying electrode and second current-carrying electrode, and that below or nearly below and between the first measuring electrode and second measuring electrode, using results of the first measurement and the second measurement.

* * * * *